US005753261A

United States Patent [19]

Fernandez et al.

[11] Patent Number: 5,753,261
[45] Date of Patent: May 19, 1998

[54] LIPID-COATED CONDENSED-PHASE MICROPARTICLE COMPOSITION

[75] Inventors: Julio M. Fernandez, Rochester; Mark B. Knudson, Shoreview, both of Minn.

[73] Assignee: Access Pharmaceuticals, Inc., Dallas, Tex.

[21] Appl. No.: 443,402

[22] Filed: May 17, 1995

Related U.S. Application Data

[63] Continuation-in-part of Ser. No. 250,646, filed as PCT/US94/01924, Feb. 19, 1994, which is a continuation-in-part of Ser. No. 17,681, Feb. 12, 1993, abandoned.

[51] Int. Cl.[6] .................................................. A61K 9/127
[52] U.S. Cl. ........................ 424/450; 424/489; 424/490
[58] Field of Search ............................ 424/450, 489, 424/484, 485, 486, 487, 488, 499, 500, 501, 1.21, 9.4; 428/402.2

[56] References Cited

U.S. PATENT DOCUMENTS

| | | | |
|---|---|---|---|
| 4,140,121 | 2/1979 | Kuhl et al. | 604/891.1 |
| 4,140,122 | 2/1979 | Kuhl et al. | 604/891.1 |
| 4,577,642 | 3/1986 | Stokes | 607/120 |
| 4,639,244 | 1/1987 | Rizk et al. | 604/19 |
| 4,869,270 | 9/1989 | Ueno et al. | 128/844 |
| 4,880,429 | 11/1989 | Stone | 623/18 |
| 4,912,032 | 3/1990 | Hoffman et al. | 435/7 |
| 5,008,102 | 4/1991 | York | 424/59 |
| 5,008,253 | 4/1991 | Casu et al. | 514/54 |
| 5,041,841 | 8/1991 | Heil, Jr. | 604/891.1 |
| 5,062,841 | 11/1991 | Siegel | 604/891.1 |
| 5,104,662 | 4/1992 | Kalsta et al. | 424/451 |
| 5,149,543 | 9/1992 | Cohen et al. | 424/499 |
| 5,188,826 | 2/1993 | Chandrasekaran | 424/78.04 |
| 5,192,535 | 3/1993 | Davis et al. | 424/78.04 |
| 5,464,629 | 11/1995 | Monshipouri | 424/450 |

OTHER PUBLICATIONS

Abe, T., et al., "Synthesis and characterization of Thermo-Sensitive Polymeric Beads," *Journal of Applied Polymer Science* 40:1223-1235 (1990).

Aitken, M.L., and P. Verdugo, "Donnan mechanism of mucin release and conditioning in goblet cells: the role of polyions," *Soc. Exp. Biol.*: 73-80 (1989).

Almers, W., "Exocytosis," *Annu. Rev. Physiol.* 52:607-624 (1990).

Annaka, M., and T. Tanaka, "Multiple phases of polymer gels," *Nature* 355:430-432 (1992).

Antonietti, M., and H. Sillescu, "Self-Diffusion of Polystyrene Chains in Networks," *Macromolecules* 18:1162 (1985).

Arshady, R., "Microspheres for biomedical applications: preparation of reactive and labelled microspheres," *Biomaterials* 14(1):5-15 (1993).

Breckenridge, L.J., and W. Almers, "Currents through the fusion pore that forms during exocytosis of a secretory vesicle," *Nature* 328:814-817 (1987).

Breckenridge, L.J., and W. Almers, "Final steps in exocytosis observed in a cell with giant secretory granules," *Proc. Natl. Acad. Sci. USA* 84:1945-1949 (1987).

Candau, F., et al., "Kinetic Study of the Polymerization of Acrylamide in Inverse Microemulsion," *J. Poly Sci. Part A*, 23:193 (1985).

(List continued on next page.)

*Primary Examiner*—Gollamudi S. Kishore
*Attorney, Agent, or Firm*—Peter J. Dehlinger; Judy M. Mohr

[57] ABSTRACT

A microparticle composition for use in compound delivery, when the composition is exposed to a selected target stimulus related to pH, temperature, radiation, or the presence of a selected ligand or ion-channel activator, is disclosed. The composition includes a condensed-phase particle matrix containing the compound to be delivered in entrapped form, and a stimulus-responsive lipid bilayer membrane formed around the matrix. Localized perturbation of the lipid membrane, and influx of monovalent counterions into the polymer matrix, in response to the selected target stimulus, causes matrix swelling and compound release from the particles.

20 Claims, 15 Drawing Sheets

OTHER PUBLICATIONS

Chevalier, P., et al., "Comparative study on the diffusion of an IgG from various hydrogel beads," *Biotechnology Techniques* 1(3).:201–206 (1987).

Clark, A.H., and S.B. Ross–Murphy, "Structural and mechanical properties of biopolymer gels," *Adv. in Polymer Sci.* 83: 57–66 (1987).

Curran, M.J., and M.S. Brodwick, "Ionic Control of the Size of the Vesicle Matrix of Beige Mouse Mast Cells," *J. Gen. Physiol.* 98: 771–790 (1991).

Cussler, E.L., et al., "Gels as size selective extraction solvents," *AIChE J.* 30: 578–582 (1984).

Drobnik, J., et al., "Synthetic model polymers in the study of protein immobilization on glycidyl methacrylate carriers," *Enzyme Microb. Technol.* 1: 108–112 (1979).

Duzgunes, N., and P.L. Felgner, "Intracellular Delivery of Nucleic Acids and Transcription Factors by Cationic Liposomes," *Methods in Enzymology* 221: 303–306 (1993).

Edwards, S.F., "Sixth International Congress of Biorheology Plenary Lecture: The Theory of Macromolecular Networks," *Biorheology* 23: 589–603 (1986).

Fernandez, J.M., et al., "Reversible condensation of mast cell secretory products in vitro," *Biophys. J.* 59: 1022–1027 (1991).

Fujimoto, K., et al., "Fluorescence Analysis for Thermosensitive Hydrogel Microspheres," *Polymer International* 30: 237–241 (1993).

Fujimoto, K., et al., "Interactions between Thermosensitive Hydrogel Microspheres and Proteins," *Journal of Intelligent Material Systems and Structures* 4: 184–189 (1993).

Gao, K., and L. Huang, "Solid core liposomes with encapsulated colloidal gold particles," *Biochimica et Biophysica Acta* 897: 377–383 (1987).

Gehrke, S.H., and E.L. Cussler, "Mass transfer in pH–sensitive Hydrogels," *Chem. Eng. Sci.* 44: 559–566 (1989).

Glenn, J.S., et al., "Delivery of Liposome–Encapsulated RNA to Cells Expressing Influenza Virus Hemagglutinin," *Methods in Enzymology* 221: 327–339 (1993).

Helfferich, F., "Preparation Cation Exchangers," in *Ion Exchange* (New York, McGraw–Hill, 1962, pp. 35–43).

Roffman, A.S., "Thermally reversible hydrogels containing biologically active species," in *Polymers in Med. III* (Migliarese, C., et al., eds., Elsevier Sci. Pub., Amsterdam, pp. 161–162, 1988).

Hoffman, A.S., "Molecular Bioengineering of Biomaterials in the 1990s and Beyond: A Growing Liaison of Polymers with Molecular Biology," *Artificial Organs* 16(1): 43–49 (1992).

Hoffman, A.S., "Environmentally Sensitive Polymers and Hydrogels. Smart Biomaterials," *MRS Bulletin September*: 42–46 (1991).

Hoffman, A.S., "Applications of Thermally Reversible Polymers and Hydrogels in Therapeutics and Diagnostics," *Journal of Controlled Release* 6: 297–305 (1987).

Hoke, F., "'Smart' Materials Research Expands Beyond Defense Arena," *The Scientist, April 27*: 13 (1992).

Hosaka, S., et al., "Preparation of Microspheres of Poly (Glycidyl Methacrylate) and Its Derivatives as Carriers for Immobilized Proteins," *Immunological Communications* 12(5): 509–517 (1983).

Huang, Y., et al., "Synthesis and characterization of bisacrylamide microgels containing sulfo groups," *Makromol. Chem.* 186: 273 (1985).

Ilmain, F., et al., "Volume transition in a gel driven by hydrogen bonding," *Nature* 349: 400–401 (1991).

Ishihara, K., et al., "Controlled release of organic substances sing polymer membrane with responsive function for amino compounds," *J. Appl. Polym. Sci.* 29: 211–217 (1984).

Janmey, P.A., et al., "Resemblance of actin–binding protein/actin gels to covalently crosslinked networks," *Nature* 345: 89–92 (1990).

Kajiwara, K., and S.B. Ross–Murphy, "Synthetic gels on the move," *Nature* 355: 208–209 (1992).

Kalvakolanu, D.V.R., and A. Abraham, "Preparation and Characterization of Immunoliposomes for Targeting of Antiviral Agents," *BioTechniques* 11(2): 218–225 (1991).

Kamei, S., et al., "Production of Anomalous Particles in the Process of Emulsifier–Free Emulsion Copolymerization of Styrene and 2–Hydroxyethyl Methacrylate," *Journal of Polymer Science Part A*, vol. 24: 3109–3116 (1986).

Kawaguchi, H., et al., "Hydrogel Microspheres II. Precipitation Copolymerization of Aerylamide with Comonomers to Prepare Monodisperse Hydrogel Microspheres," *Polymer Journal* 23(8): 955–962 (1991).

Kawaguchi, H., et al., "Preparation and Modification of Monodisperse Hydrogel Microspheres," *Polymer International* 30: 225–231 (1993).

Kawaguchi, H., et al., "Hydrogel microspheres III. Temperature–dependent adsorption of proteins on poly–N–isopropylacrylamide hydrogel microspheres," *Colloid and Polymer Science* 270(1): 53–57 (1992).

Kerkam, K., et al., "Liquid crystallinity of natural silk secretions," *Nature* 349: 596–598 (1991).

Kibat, P.G., et al., "Enzymatically activated microencapsulated liposomes can provide pulsatile drug release," *The FASEB Journal* 4: 2533–2539 (1990).

Kim, T.D., et al., "Studies on Liposome–Encapsulated Heparin," *Thrombosis Research* 43: 603–612 (1986).

Kishi, R., and Y. Osada, "Reversible Volume Change of Microparticles in an Electric Field," *J. Chem. Soc., Faraday Trans.* 1, 85(3): 655–662 (1989).

Klein, J., et al., "Forces between polymer–bearing surfaces undergoing shear," *Nature* 352: 143–145 (1991).

Kokufata, E., et al., "Saccharide–sensitive phase transition of a lectin–loaded gel," *Nature* 351: 302–304 (1991).

Kreuter, J., "Nanoparticles—Preparation and Applications," Chapter 6 from *Microcapsules and Nanoparticles in Medicine and Pharmacy* (M. Donbrow, ed., CRC Press Florida, 1992, pp. 125–148).

Kuhn, W., et al., "Reversible dilation and contraction by changing the state of ionization of high–polymer acid networks," *Nature* 165: 514–516 (1950).

Kwon, G.S., et al., "Release of proteins via ion exchange from albumin–heparin microspheres," *Journal of Controlled Release* 22: 83–94 (1992).

Kwon, I.C., et al., "Electrically erodible polymer gel for controlled release of drugs," *Nature* 354: 291–293 (1991).

Langer, R., "New Methods of Drug Delivery," *Science* 249: 1527–1532 (1990).

Lasic, D.D., et al., "Gelation of liposome interior. A novel method for drug encapsulation," *FEBS Letters* 312(2,3): 255–258 (1992).

Lifshitz, I.M., et al., "Some problems of the statistical physics of polymer chains with volume interaction," *Rev. of Mod. Phys.* 50: 683–713 (1978).

Margel, S., et al., "Polyacrolein Microspheres as a New Tool in Cell Biology," *J. Cell Sci.* 56: 157–175 (1982).

Monck, J.R., et al., "Is swelling of the secretory granule matrix the force that dilates the exocytotic fusion pore?" *Biophys. J. 59*: 39–47 (1992).

Morita, Y., et al., "New functional microspheres with active succinimide groups," *Colloid & Polymer Sci. 265*: 916–921 (1987).

Nakamae, K., et al., "Swelling behavior of hydrogels containing phosphate groups," *Makromol. Chem. 193*: 983–990 (1992).

Nanavati, C., et al., "The Secretory Granule Matrix: A FastActing Smart Polymer," *Science 259*: 963–965 (1993).

Nishio, I., et al., "Critical density fluctuations within a single polymer chain," *Nature 300*: 243–244 (1982).

Nishio, I., et al., "First observation of the coil–globule transition in a single polymer chain," *Nature 281*: 208–209 (1979).

Nustad, K., et al., "Monodisperse Polymer Particles in Immunoassays and Cell Separation," Chapter 4 from *Microspheres: Medical and Biological Applications* (A. Rembaum et al., eds., CRC Press Florida 1988, pp. 53–75).

Okahata, Y. et al., "Thermoselective permeation from a polymer–grafted capsule membrane," *Macromolecules 19*: 493–494 (1986).

Okano, T., et al., "Thermally On–Off Switching Polymers for Drug Permeation and Release," *Journal of Controlled Release 11*: 255–265 (1990).

Okubo, M., et al., "Production of Anomalous 'Golf Ball–Like' Composite Polymer Particles by Seeded Emulsion Polymerization," *Chemistry Express 8(4)*: 253–256 (1993).

Okubo, M., et al., "Production of Multihollow Polymer Particles by Stepwise Alkali–Acid Method," Chapter 18, *Polymer Latexes: Preparation, Characterization, and Applications* (E.S. Daniels, et al., eds., American Chemical Society 1992, pp. 282–288).

Okubo, M., and T. Nakagawa, "Preparation of micron–size monodisperse polymer particles having highly crosslinked structures and vinyl groups by seeded polymerization of divinylbenzene using the dynamic swelling method," *Colloid Polym. Sci. 270*: 853–858 (1992).

Osada, Y., "Conversion of Chemical Into Mechanical Energy by Synthetic Polymers (Chemomechanical Systems)," *Advances in Polymer Science 82*: 1–46 (1987).

Ostro, M.J., and P.R. Cullis, "Use of liposomes as injectable–drug delivery systems," *American Journal of Hospital Pharmacy 46*: 1576–1587 (1989).

Park, T.G., and A.S. Hoffman, "Immobilization of *Arthrobacter simplex* in a thermally reversible hydrogel: effect of temperature cycling on steroid conversion," *Biotech. and Bioeng. 35*: 152–159 (1990).

Park, T.G., and A.S. Hoffman, "Preparation of Large, Uniform Size Temperature-Sensitive Hydrogel Beads," *Journal of Polymer Science Part A, vol. 30*: 505–507 (1992).

Pekarek, K.J., et al., "Double-walled polymer microspheres for controlled drug release," *Nature 367*: 258–260 (1994).

Pelton, R.H., "Polystyrene and Polystyrene–butadiene Latexes Stabilized by Poly (N–isopropylacrylamide)," *Journal of Polymer Science Part A, vol. 26*: 9–18 (1988).

Pelton, R.H., and P. Chibante, "Preparation of Aqueous Latices with N–Isopropylacrylamide," *Colloids and Surfaces 20*: 247–256 (1986).

Radomsky, M.L., et al., "Macromolecules released from polymers: diffusion into unstirred fluids," *Biomater. 11*: 619–624 (1990).

Randolph, T.W., et al., "Sub–Micrometer–Sized Biodegradable Particles of Poly(L–Lactic Acid) via the Gas Antisolvent Spray Precipitation Process," *Biotechnol. Prog. 9*: 429–435 (1993).

Siegel, R.A., and B.A. Firestone, "pH–dependent equilibrium swelling properties of hydrophobic polyelectrolyte copolymer gels," *Macromolecules 21*: 3254–3259 (1988).

Straubinger, R.M., "pH–Sensitive Liposomes for Delivery of Macromolecules into Cytoplasm of Cultured Cells," *Methods in Enzymology 221*: 361–376 (1993).

Streifel, J.A., "Microspheres and Cell Separation," Chapter 5 from *Microspheres: Medical and Biological Applications* (A. Rembaum et al., eds., CRC Press Florida 1988, pp. 77–88).

Suzuki, A., and T. Tanaka, "Phase transition in polymer gels induced by visible light," *Nature 346*: 345–347 (1990).

Szoka, F., and D. Papahadjopoulos, "Comparative Properties and Methods of Preparation of Lipid Vesicles (Liposomes)," *Ann. Rev. Biophys. Bioeng. 9*: 467–508 (1980).

Szoka, F., and D. Papahadjopoulos, "Procedure for preparation of liposomes with large internal aqueous space and high capture by reverse–phase evaporation," *Proc. Natl. Acad. Sci. USA 75*: 4194–4198 (1978).

Tai, E.F., "Precipitation Polymerization of Acrylamide Using Vazo–33 as an Initiator and Acetonitrile/Water Mixtures As the Solvent," *J. Poly. Sci. Part A, 24*: 567–577 (1986).

Tam, P.Y., and P. Verdugo, "Control of mucus hydration as a Donnan equilibrium process," *Nature 292*: 340–342 (1981).

Tanaka, H., et al., "Diffusion Characteristics of Substrates in Ca–Alginate Gel Beads," *Biotechnology and Bioengineering 26*: 53–58 (1984).

Tanaka, T., "Collapse of gels and the critical endpoint," *Phys. Rev. Lett. 40*: 820–823 (1978).

Tanaka, T., et al., "Phase transitions in ionic gels," *Phys. Rev. Lett. 45*: 1636–1639 (1980).

Tanaka, T., et al., "Collapse of Gels in an Electric Field," *Science 218*: 467–469 (1982).

Tanaka, T., and D.J. Fillmore, "Kinetics of swelling of gels," *J. Chem. Phys. 70(03)*: 1214–1218 (1979).

Urry, D.W., et al., "Chemical potential driven contraction and relaxation by ionic strength modulation of an inverse temperature transition," *J. Am. Chem. Soc. 110*: 3303–3305 (1988).

Vanderhoff, M.S., et al., "Preparation of Large–Particle–Size Monodisperse Latexes in Space," *Polym. Matr. Sci. Eng. 54*: 587–592 (1986).

Verdugo, P., et al., "Molecular Mechanism of Product Storage and Release in Mucin Secretion. II. The Role of Extracellular $Ca^{++}$," *Biorheology 24*: 625–633 (1987).

Weiner, A.L., et al., "Liposome–Collagen Gel Matrix: A Novel Sustained Drug Delivery System," *Journal of Pharmaceutical Sciences 74(9)*: 922–925 (1985).

Williams, C., et al., "Polymer collapse," *Ann. Rev. Phys. Chem. 32*: 433–451 (1981).

Yoneda, Y., "Microinjection of Macromolecules into Cultured Cells by Erythrocyte Ghost–Cell Fusion," *Methods in Enzymology 221*: 306–317 (1993).

Yui, N., et al., "Inflammation responsive degradation of crosslinked hyaluronic acid gels," *Journal of Controlled Release 22*: 105–116 (1992).

Yui, N., et al., "Photo–responsive degradation of heterogeneous hydrogels comprising crosslinked hyaluronic acid and lipid microspheres for temporal drug delivery," *Journal of Controlled Release 26*: 141–145 (1993).

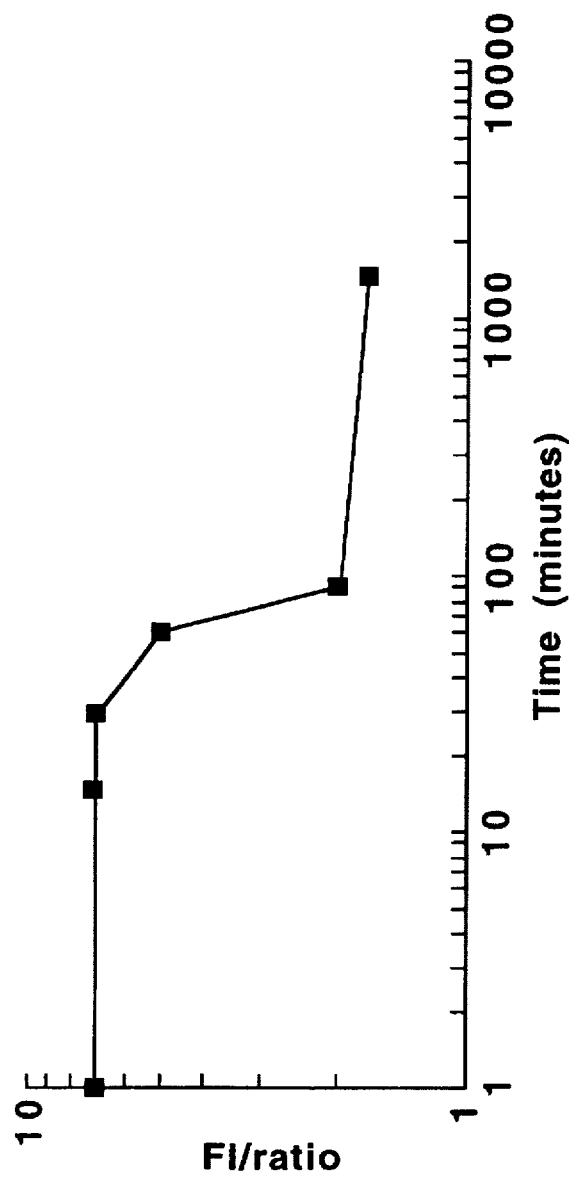

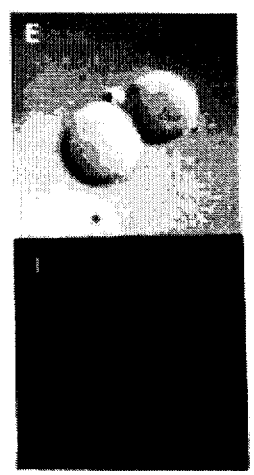
Fig. 8A
Fig. 8B
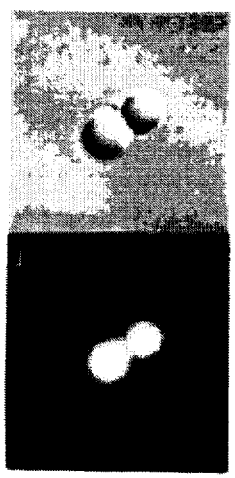
Fig. 8C
Fig. 8D
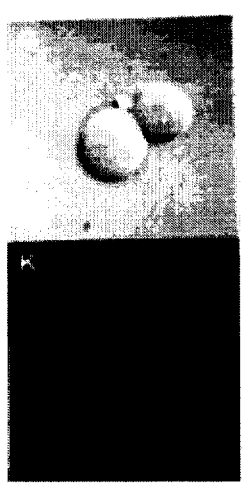
Fig. 8E
Fig. 8F
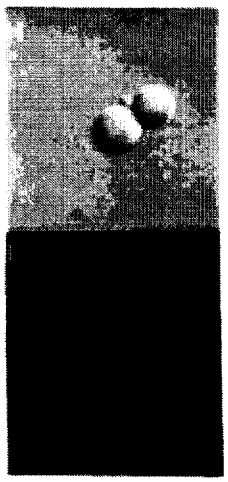
Fig. 8G
Fig. 8H $Ca^{++}$

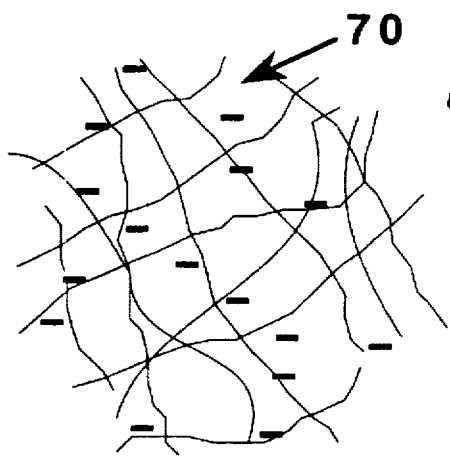
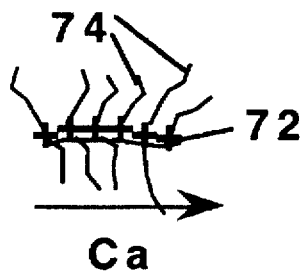
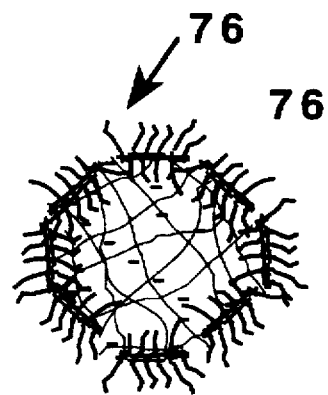
Fig. 12A
Fig. 12B
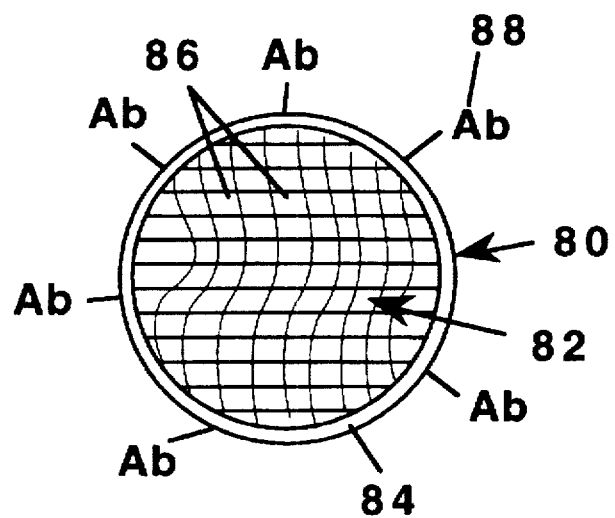
Fig. 13

+ Stimulus

Acid or hγ + ROS
or high-energy hγ

To Fig. 17C

LIPID-COATED CONDENSED-PHASE MICROPARTICLE COMPOSITION

This application is a continuation-in-part of U.S. patent application Ser. No. 08/250,464, filed May 27, 1994, which is a continuation-in-part of U.S. application Ser. No. 08/017,681, filed Feb. 12, 1993, now abandoned. The present application and application Ser. No. 08/250,464 also claim priority to PCT application Ser. No. WO US94/01924, filed Feb. 19, 1994.

1. FIELD OF THE INVENTION

The present invention relates to condensed-phase polymer-matrix microparticles designed for cascade-like triggered release of a therapeutic agent entrapped in the microparticles, when the microparticles are delivered to a selected target site.

2. REFERENCES

Antonietti, M., et al., *Macromolecules*, 18:1162 (1985).

Arshady, R., *Biomaterials* 14(1):5-20 (1993).

Cadan, F., et al., *J. Poly Sci.*, Part A, 23:193 (1985).

Hosaka, S., et al., *Immunological Communications* 12(5):509-517 (1983).

Huang, Y., et al., *Makromol. Chem.*, 186:273 (1985).

Hucho, F., Ed., *NEUROTRANSMITTER RECEPTORS*, Vol. 24, 1-59 (1993).

Kamei, S., et al., *J. Polymer Sci.: Part A: Polymer Chem.* 24:3109-3116 (1986).

Kawaguchi, H., et al., *Polymer J.* 23(8):955-962 (1991).

Kawaguchi, H., et al., *Colloid and Polymer Sci.* 270(1):53 (1992).

Kawaguchi, H., et al., *Polymer Int.* 30:225-231 (1993).

Klaerke, D. A., et al., *J. Membrane Biology* 95:105-112 (1987).

Kreuter, J., in *MICROCAPSULES AND NANOPARTICLES IN MEDICINE AND PHARMACY*, CRC Press, Boca Raton Fla. (1992).

Margel, S., et al., *J. Cell Sci.* 56:157-175 (1982).

Okubo, M., et al., in "Production of Multihollow Polymer Particles by Stewise Alkali-Acid Method" in *POLYMER LATEXES* (Daniels, E. S., et al., eds.) American Chemical Society, Washington D.C. (1992).

Okubo, M., and Nakagawa, T., *Collid Polym. Sci.* 270:853-858 (1992).

Pelton, R. H., and Chibante, P., *Colloids and Surfaces* 20:247-256 (1986).

Pelton, R. H., *J. Polym. Sci.: Part A: Polym. Chem.* 26:9-18 (1988).

Szoka, F., et al., *Ann. Rev. Biophys. Bioeng.* 9:467 (1980).

Szoka, F., et al., *Proc Nat Acad Sci, USA* 75:4194 (1978).

Tai, E. F., *J Poly Sci.*, Part A, 24:567 (1986).

Tanaka, H., et al., *Biotech. and Bioeng.* 26:53-58 (1984).

Vanderhoff, M. S., et al., *Polym. Matr Sci Eng.*, 54:587 (1986)

Wong, S. S., *CHEMISTRY OF PROTEIN CONJUGATION AND CROSSLINKING*, CRC Press, Boca Raton, Fla. (1991).

Yui, N., et al., *J. Controlled Rel.* 22:105-116 (1992).

3. BACKGROUND OF THE INVENTION

The use of synthetic polymers in drug delivery devices has focused on "smart polymers" a term ascribed to polymers which form gels that have the ability to expand or contract in response to a specific stimulus, such as light, temperature or pH. Typically, such polymers will precipitate in solution or collapse with concomitant expulsion of gel pore contents. In some cases, these processes are reversible.

Synthetic polymers may be based on a number of types of monomeric units, including vinyl monomers, N-alkyl substituted acrylamides and the like. Copolymers have also been utilized in an attempt to combine or modulate the stimulus responsive properties of one or more known smart polymers.

4. SUMMARY OF THE INVENTION

The present invention includes, in one aspect, a particle composition for rapid release of a compound, when the composition is exposed to a selected target stimulus related to pH, temperature, or the presence of a selected ligand. The composition includes encapsulated, condensed-phase microparticles having an average size in a selected size range between 0.05 and 5 microns.

Each microparticle is composed of a condensed-phase matrix of crosslinked polyionic polymer filaments, and is capable of decondensing to an expanded phase when selected multivalent counterions also present within the matrix are replaced by monovalent counterions. The compound to be delivered is entrapped in the condensed-phase microparticle. The condensed-phase microparticle and entrapped drug are encapsulated within a lipid bilayer membrane. Localized perturbation of the lipid membrane, and influx of monovalent counterions into the polymer matrix, in response to the selected target stimulus, causes a cascade effect involving matrix swelling and further membrane perturbation, resulting in rapid compound release from the particles.

In one general embodiment, the composition is designed for use as a drug-delivery composition. Here the microparticles have an average size in a selected size range preferably between 0.05 and 0.5 microns, the compound is a therapeutic compound, and the lipid membrane is effective to allow influx of external counterions into the microparticle matrix when exposed to a selected stimulus in vivo.

In another specific embodiment, the polymer filaments forming the microparticle matrix are sulfated, sulfonated, carboxylated, or polyphosphated polyanionic polymers, preferably comb-polymer glycoprotein filaments, and the multivalent counterion is a multivalent cation.

Also in more specific embodiment, the encapsulated microparticles contain a concentration of solute molecules, including a therapeutic compound, that in the absence of the matrix, would produce hypertonic swelling of the encapsulated microparticle's lipid membrane in a physiological medium. Alternatively, the concentration of therapeutic compound within the encapsulated microparticles is greater than the solubility of the drug in the aqueous medium within the microparticle matrices.

The lipid bilayer membrane may include anti-ligand molecules attached to the outer membrane surface, for binding specifically to ligand antigen or antibody molecules present at an in vivo site, for producing complement-mediated lysis at the selected in vivo site. For use in delivering a drug to a site that can be heated to an elevated temperature above normal body temperature, the encapsulated microparticles' lipid membranes are formed of lipids having a phase transition temperature between the normal body temperature and the elevated temperature.

In another embodiment, the lipid membrane may include a monovalent ion-selective channel. Such a channel can be stimulated to open by a specific stimulus, depending on the type of channel selected. One particularly useful channel is a calcium-activated monovalent ion-selective channel, such as a potassium channel. When exposed to a critical extracellular calcium level, this channel will open, allowing potassium access to the condensed microparticle to effect decondensation, rupture of the encapsulating membrane and extrusion of particle contents into the extra-vesicular medium. Ligand-gated channels, such as glutamate receptors and acetylcholine receptors, can also be used to provide selective release of compound.

In another related embodiment, the encapsulated microparticles' lipid membranes may include a selected lipid effective to change conformation or structure in response to a selected stimulus. Such change results in perturbation of the vesicular membrane and consequent exposure of the condensed microparticle to monovalent ions present in the extravesicular medium, decondensation and release of vesicular contents. One type of lipid useful in the invention is a plasmalogen having a vinyl ether functional group capable of cleavage in response to acid or a reactive oxygen species. An example of such a plasmalogen is 1-alk-1'-enyl-2-palmitoyl-sn-glycero-3 phospholine.

Plasmalogen containing compositions are stimulated to release compound when introduced to an acid environment, or when placed in an environment having reactive oxygen species (ROS), such as singlet oxygen, hydroxyl radicals, hydrogen peroxide or superoxide radicals. Alternatively, ROS levels can be elevated by exposing a tissue region to X- or gamma irradiation.

Compositions containing plasmalogens may, in addition, contain a lysogenic substance that, in response to photoillumination, produces a reactive oxygen species or acid effective to cleave the vinyl ether functional group of the plasmalogen.

In another related embodiment, lipids comprising the encapsulated microparticles' lipid membranes may include a light-sensitive lipid capable of changing conformation in response to exposure to light at a predetermined wavelength. An example of such a lipid is a member of the class of retinoyl-sn-glycero-3-phosphocholine compounds.

These and other objects and features of the invention will become more fully apparent when the following detailed description of the invention is read in conjunction with the accompanying drawings.

BRIEF DESCRIPTION OF THE FIGURES

FIGS. 7A and 7B show the rate of release of doxorubicin from condensed-phase microparticles when stored in distilled water (7A), and when exposed to physiological saline (FIG. 7B);

FIGS. 8A–8H are light photomicrographs (8A, 8C, 8E, and 8G) and fluorescent micrographs (8B, 8D, 8F, 8H) of microparticles (i) before particle condensation (8A and 8B); (ii) after microparticle loading with fluorescent histamine (8C and 8D); (iii) after decondensing the fluorescent-loaded particle with $Na^+$-containing medium (8E and 8F); and after a second particle condensation with unlabeled histamine (8G and 8H);

FIGS. 12A and 12B show a method of attaching polyethleneglycol polymer chains to the exterior surface of a microparticle;

FIG. 13 shows an encapsulated microparticle for use in a compound-release composition formed in accordance with another aspect of the invention;

DETAILED DESCRIPTION OF THE INVENTION

I. Definitions

Figure 1:
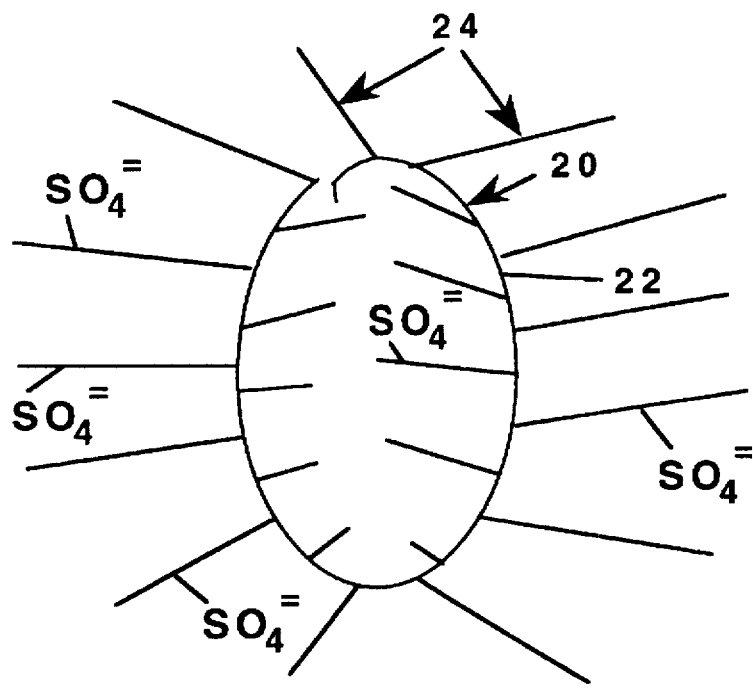
FIG. 1 shows a generalized structure of a sulfated combpolymer glycoprotein used in forming a polymer-matrix microparticle in accordance with the invention.

As used herein, the terms below have the following definitions unless indicated otherwise.

"Polyionic polymers" or "polyionic polymer filaments" are polymers containing multiple charged subunits (subunits containing at least 1 negative or positive charge at a selected pH between about 4–10), and having a net negative (polyanionic) or net positive (polycationic) charge at the selected pH.

"Polyanionic polymers" or "polyanionic polymer filaments" are polyionic polymers in which the charged subunits are ionizable, negatively charged subunits, typically sulfate, sulfonate, or carboxylate, or phosphate groups. Such polyanionic polymers or polymers filaments are also referred to herein as "sulfated, sulfonated, carboxylated, or phosphated" polymers or polymer filaments, respectively.

"Polycationic polymers" or "polycationic polymer filaments" are polyionic polymers in which the charged subunits are ionizable positively charged subunits, typically primary, secondary, tertiary amine groups or in which the charged subunits contain quaternary amine groups.

"Polyionic hydrophilic polymers" are polyionic polymers which are soluble in an aqueous solution, at a selected pH between about 3–10, preferably having a partition coefficient, expressed as log n-octanol/water, of less than zero.

"Comb polymers" or "comb-polymer filaments" are polymer filaments composed of a polymeric backbone chain and a plurality of polymer side chains attached to the backbone polymer at spaced positions along the backbone chain, and radiating outwardly from the backbone chain.

A "comb-polymer glycoprotein" refers to a comb polymer having a polypeptide backbone chain to which is attached, at spaced positions along the polypeptide chain, a plurality of anionic polysaccharide side chains.

A "sulfated, sulfonated, carboxylated, or phosphated comb-polymer glycoprotein" refers to a polyanionic comb-polymer glycoprotein in which the polysaccharide side chains carry sulfate, sulfonyl, carboxyl, or phosphate groups, respectively, at one or more sugar residues.

"Glycosaminoglycans" consist of disaccharide repeating units containing a derivative of an amino sugar (glucosamine or galactosamine) where at least one of the sugars in the disaccharide contains a carboxylate or sulfate group. Exemplary glycosaminoglycans include hyaluronate, chondroitin sulfate, keratan sulfate, heparin sulfate and heparin.

"Proteoglycan" refers to a polypeptide backbone to which is attached multiple anionic heteropolysaccharide sidechains which are generally glycosaminoglycans.

A "crosslinked polymer matrix" is a matrix of polymer filaments in which the filaments are crosslinked by covalent crosslinking between and/or among filaments by bifunctional or polyfunctional crosslinking agents, or crosslinked by ionic bonds between ionic groups on the polymer filaments and multivalent oppositely charged crosslinking species;

A "multivalent solute species" is a divalent or multivalent anionic or cationic solute species.

"Polyvalent counterions" are multivalent solute species each containing at least 3 charged groups (of the same charge), typically amine or carboxyl charged groups. Included in this definition are polypeptides, such as polylysine or polyaspartate, or proteins containing charged side chains, and nonpeptide polymers, such as polyquaternary amines, having a high density of positively or negatively charged monomer units.

A "monovalent counterion", a "divalent counterion", or a "multivalent counterion" is a monovalent, divalent, or multivalent ionic species, respectively, whose charge is opposite to that of the charge of the polymer matrix. In a matrix formed of polyanionic filaments, the counterion is a cationic species, and in a matrix formed of polycationic filaments, the counterion is an anionic species.

"Polyvalent counterions" are multivalent counterions containing at least 3 charged groups (of the same charge), typically amine or carboxyl charged groups. Included in this definition are polypeptides, such as polylysine or polyaspartate, or proteins containing a charged side chains, and nonpeptide polymers, such as polyquaternary amines, having a high density of positively or negatively charged monomer units.

"Microparticles" refer to particles which are formed of a crosslinked polyionic polymer matrix, and which have condensed-state sizes in the range between about 0.05 to 50 μm (μmeter), preferably 0.05 to 5 μm (μmeter).

"Condensed-phase microparticles" or "condensed-state microparticles" refers to microparticles in a condensed or collapsed phase. The matrix in a collapsed phase preferably contains less than about 30 percent by volume water.

"Decondensed-phase microparticles" or "decondensed-state microparticles" refers to microparticles in an expanded decondensed phase in which the particle matrix is open to diffusion of small molecules into and out of the matrix.

The "effective concentration" of a compound in a condensed-phase microparticle, expressed in mM, is the concentration of the compound expressed as moles compound/volume condensed-phase microparticle, calculated from the known size of the condensed-phase particle.

II. Polymer-Matrix Microparticles

This section describes the preparation and properties of polymer-matrix microparticles used in various aspects of the invention.

The microparticles are composed of crosslinked polyionic filaments, and preferably a crosslinked network of polyanionic filaments, such as sulfated, sulfonated, or carboxylated polymers, including comb-polymer glycoproteins. Exemplary polymer filaments, and methods of preparing the crosslinked matrices, either by isolation from biological sources, or by synthetic means, will be described below.

According to an important aspect of the invention, the particles can be cycled rapidly between condensed and decondensed states or phases, by changing the ionic environment of the microparticles. In the condensed phase, the microparticles are relatively dense and opaque, and preferably contain less than about 30 percent by volume water, and preferably less than about 5–15 percent by volume. The condensed-phase microparticles have preferred average sizes in the size range between 0.05 and 50 μm (micrometer), preferably 0.05 to 10 Mm, and 0.05 to 0.5 μm for therapeutic uses.

A. Isolation of Microparticles

Microparticles suitable for use in the methods and compositions of the invention may be isolated from one or more suitable biological sources, including cultured cells, as described below. In certain embodiments of the invention, microparticles are isolated as the intact cores of secretory granules. Such granules are typically composed of a membrane surrounding a core of highly charged biopolymers. Proteoglycans, as found in mast cell granules are particularly preferred for forming polymer-matrix microparticles for use in various embodiments of the invention described herein. Glycoproteins, such as form mucous, may also be useful in forming microparticles for certain applications.

Secretory granules can be obtained from mast cells, goblet cells, chromaffin cells and other secretory cells, according to the particular biopolymer and chemical properties required. For example, goblet cell granules contain mucin, a mixture of linear polyanionic glycoproteins, whereas mast cell granules contain heparin proteoglycans, which contain ester sulfate groups. Biopolymers isolated from each of these sources have different characteristics. Mucin-containing granules decondense to form a diffuse gel, while mast cell-derived heparin proteoglycan particles maintain a particulate form following decondensation. Other secretory granule derived materials include, but are not limited to, chromogranin A from chromaffin granules of the adrenal medulla and acidic protein SP-1 from parathyroid granules. In addition, polyanionic chromogranin A-like matrices are present in secretory cells of the thyroid, pancreatic islet cells, sympathetic ganglia, anterior pituitary and gastric antrum.

Preferred isolation techniques for secretory granules from cells include homogenizing the cells with a mechanical homogenizer, treating the cells with detergents, rupturing the cells by sonication, or combinations thereof. The homogenizing or sonicating conditions may leave the granule membranes substantially intact on the granules. Alternatively, cells may be stimulated to release the secretory granules, such as by contact with a releasing agent.

Preferably, to form biological microparticles for use in the invention, the mast-cell membranes will be removed, either during the isolation process, or by detergent means thereafter, as described for mast cell granules in Example 1. After the secretory granules are released from the ruptured cells, the granules are then separated from the cell debris by centrifugation in a density gradient, for example, a sucrose gradient or a metrizamide gradient. Such cell rupturing and centrifugation procedures are well known in the art.

Preferred secretory granules for isolation of polymer-matrix microparticles include mast cell granules. Mast cells can be obtained from the peritoneal cavity of various rodent species. Adult beige mice ($bg^J/bg^J$, Jackson Laboratories, Bar Harbor, Me.) are particularly convenient sources of such cells, as described in Example 1. Cells are collected by peritoneal lavage, and the isolated cells are equilibrated in an isosmotic "extracellular" solution. Cells are stimulated to secrete granules, by use of a secretagogue, such as compound 48/80, or by mild sonication, as detailed in Example 1.

These alternative methods of stimulating release of granules from secretory cells result in differences in initial appearance of the granules. Granules released by stimulation with Compound 48/80 decondense rapidly upon release, but can be recondensed to within 5% of original intracellular volume by immersion, for example in a solution containing 50 mM histamine, pH 3. Granules isolated by mild sonication retain an intact granule membrane and their condensed form. Membranes enclosing the granules may then be removed by conventional techniques such as detergent treatment (e.g., Triton X 100) or strong sonication.

Mucin containing secretory granules may be isolated from secretory cells located in the respiratory system called "Goblet" cells. When released from the granules, mucins undergo massive swelling to form a gel in aqueous solution. (Verdugo) Mucin particles can be isolated from primary cultures of Goblet cells from rabbit trachea, according to standard methods. Such cultured cells spontaneously degranulate in a manner similar to mast cells. Upon release from the cell, mucin-containing granules swell rapidly for 5–10 sec. The granules generally anneal with each other in the extracellular fluid. The swelling process can be retarded significantly by elevation of calcium content in the extracellular medium (Verdugo).

B. Synthetic Microparticles

Polymer-matrix microparticles having the rapid condensation/decondensation properties described above can also be made synthetically by a variety of methods. The microparticles are made by cross-linking polyionic hydrophilic polymers under conditions which lead to cross-linked matrices in the 0.05 to 50 μm, preferably 0.05 to 5 μm particle-size range, when the particles are in their condensed phases.

C. Filament Preparation and Crosslinking

Below are described two general methods for producing polyionic filament components in the microparticles.

1. Prepolymerized Ionic Polymer Filaments

In one embodiment, the microparticles are prepared by crosslinking existing ionic polymer filaments. Polymer filaments that are suitable include sulfated, sulfonated, carboxylated, or phosphated hydrophilic polymers, in forming negatively charged polymer matrices, and amine-containing hydrophilic polymers, in forming positively charged polymer matrices.

Preferred polyanionic polymer filaments include sulfated proteoglycans, e.g., sulfated heparin, and other sulfated polysaccharides, such as sulfated cellulose or cellulose derivatives, carrageenin and dextran sulfate, mucin, sulfated polypeptides, such as polylysine with sulfated amine groups, and glycopeptides with sulfonate-derivatized saccharide or peptide subunits, and hyaluronic acid.

Figure 2A:
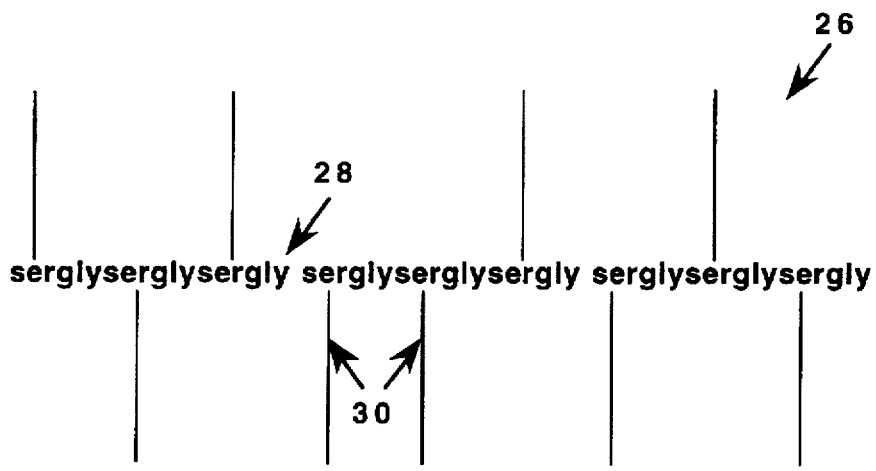
FIGS. 2A and 2B show the backbone structure of a heparin sulfate proteoglycan polymer (FIG. 2A), and the side chain structure of the same polymer (FIG. 2B)

One type of preferred polyanionic polymer filament includes sulfated, sulfonated, carboxylated, or phosphated comb-polymer glycoproteins. The basic structure of this type of polymer is shown in FIG. 1. The polymer, indicated at 20, generally includes a polymeric backbone 22, such as a polypeptide, such as one having repeating subunits, such as repeating amino acid subunits. Attached to the backbone, at attachment points spaced along the backbone, are a plurality of polysaccharide side chains, such as side chains 24. The side chains carry negatively charged sulfate groups, as shown, typically several per chain, but an average of at least about 1 negatively charged group per chain.

Where the backbone polymer contains amino acid residues, the subunit side chains may have a variety of selected chemically reactive groups, such as a hydroxyl, carboxy, or amino groups, by which the side chains of the comb-polymer can be attached to the polymer, such as illustrated for the SER-GLY repeat backbone shown in FIG. 2A.

If the comb-polymer can be prepared de novo, a variety of coupling reaction are available for attaching the side chains covalently to the backbone polymer. In general, this is done by activating one end of the polysaccharide side chains, and reacting the activated chains with a backbone under conditions effective to couple the activated chains to corresponding reactive side-chain groups on the polypeptide or other polymer backbone. Coupling reactions suitable for coupling to carboxy, hydroxyl, amino, or sulfhydryl groups are well known.

The percentage of backbone reactive groups, and the relative lengths and stoichiometry of the polymer filament backbone chain and side chains is preferably such that the comb-polymer preferably includes at least about 80–95% by weight polysaccharide components.

Figure 2B:
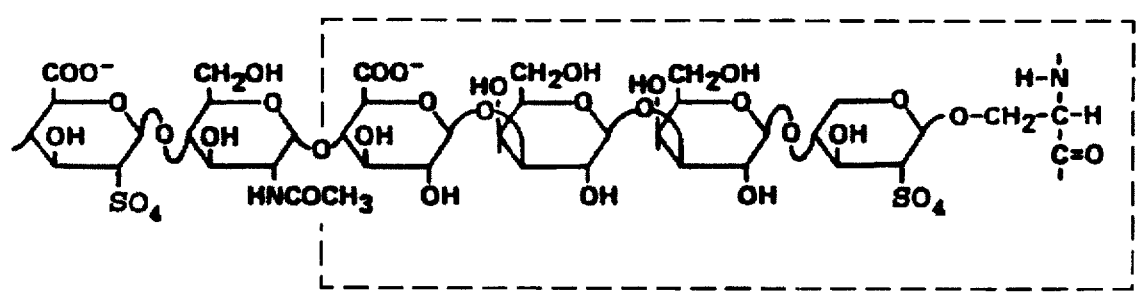

One preferred sulfated comb-polymer glycoprotein is heparin sulfate proteoglycan, whose structure is indicated in FIG. 2A. As seen, the polymer (indicated at 26) has a polypeptide backbone 28 composed of repeating SER-GLY dipeptide subunits, with heparin chains, such as side chains 30, attached to the backbone at some of the SER residues, through the SER hydroxyl group. A portion of a heparin side chain is shown in FIG. 2B.

Proteoglycan polymer filaments of this type may be synthesized following known methods, such as those outlined above. Alternatively, some proteoglycan filaments, such as heparin sulfate proteoglycan, can be obtained by isolation from biological sources.

The preformed filaments may be crosslinked by bifunctional or multifunctional crosslinking agents effective to form intermolecular links between the filaments. In one general embodiment, the crosslinking agent may be long, hydrophilic polymer chain, such as a polyethyleneglycol (PEG) chain, having activated end groups effective to form covalent linkages to selected reactive groups on the polysaccharide side chains of the polymer filaments.

Figure 3:
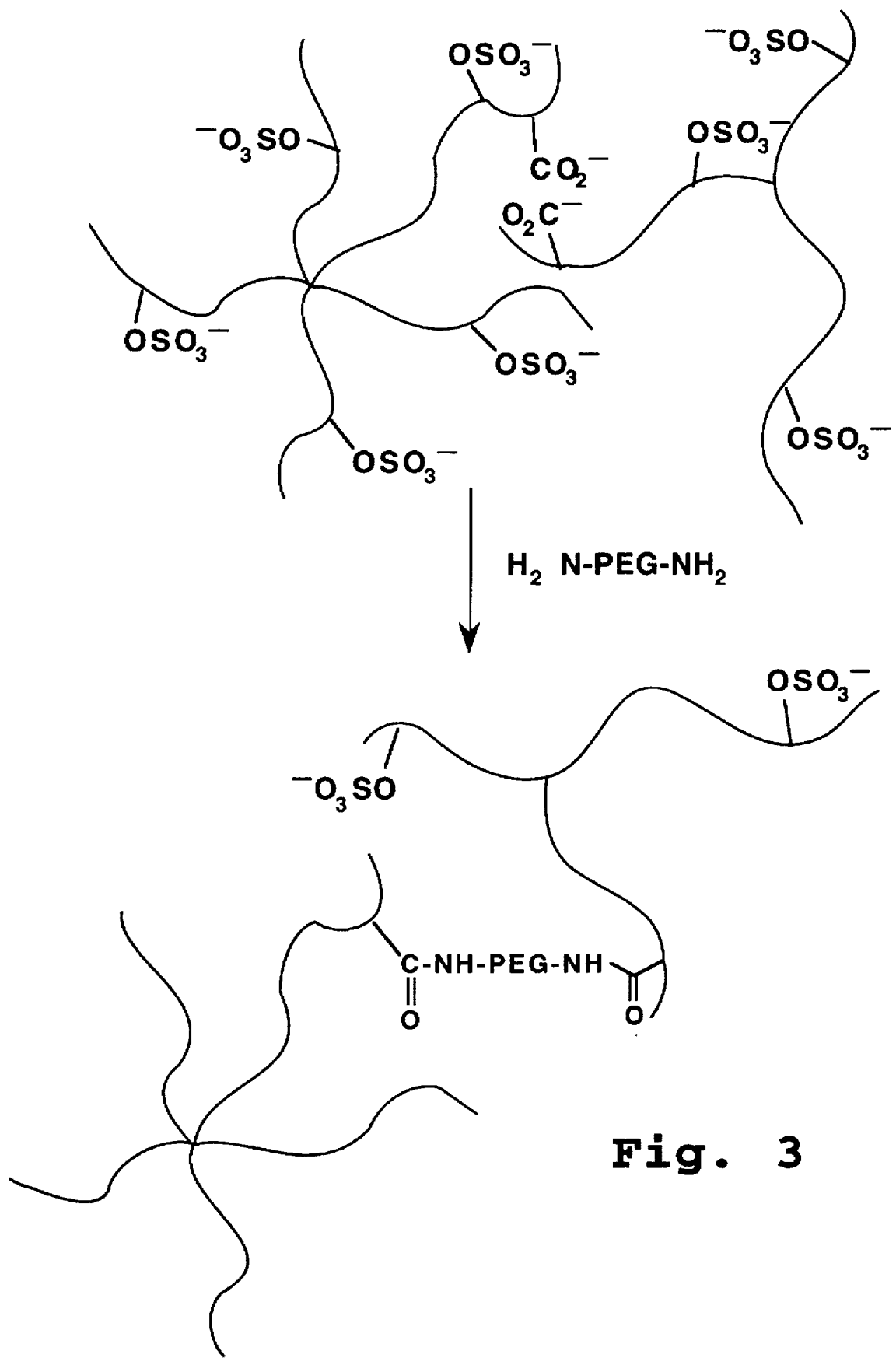
FIG. 3 shows a crosslinking reaction used in forming a crosslinked polymer matrix for use in the invention.

FIG. 3 illustrates one exemplary crosslinking reaction in which carboxyl groups in sulfated heparin side chains, such as shown at top in the figure, are linked by an activated diamino-PEG molecule, as indicated. Methods for activating crosslinking agents of this type, and for crosslinking polymer filaments by the activated agents, are well known (Wong, Antonietti, Huang, Funke). Alternatively, the carboxyl groups may be activated, for reaction with free amine groups in the crosslinking polymer.

The crosslinking reaction is preferably one which can be initiated by heat, e.g., by raising the temperature of the reaction by infrared irradiation, or by radiation, such as visible light, UV or X-irradiation, according to known polymer forming reactions.

2. Polymer Synthesis

In another general embodiment, the charged polymer filaments are formed de novo in a polymerization and crosslinking reaction. A variety of monomer systems for forming crosslinked microparticles have been proposed, for example vinylpyridine, 2-hydroxyethyl methacrylate, acrylamide, dimethylacrylamide, acrolein, poly(N-isopropylacrylamide, amino acid monomers, saccharide monomers, alkylcyanoacrylates, glycidyl methacrylate, and hyaluronic acid (e.g., Wu, Arshady, Margel, Okubo, 1992a, 1992b, Kreuter, Kamei, Fujimoto, Yui, and Hosaka).

These monomers are mixed with selected charged-group monomers, such as methacrylic acid, vinyl monomers having carboxyl or amine groups (Arshady) or monomers in which the reactive group has been converted to a sulfate, sulfonate, or phosphate group, by standard reaction methods. Typically, the charged monomer will be included in a range from about 5–50 mole percent of uncharged monomer, although the polymer may be formed entirely from charged monomer units.

The polymerized chains may be crosslinked by free radical polymerization, by inclusion of crosslinking monomers, such as methylene-bis-acrylamide or divinylbenzene (e.g., Okubo, Arshady, Kreuter), or by crosslinking through polymer chains, as above.

In both of the approaches discussed above, the polymer filaments may be modified, before or after crosslinking to form microparticles, to introduce charged groups, and/or binding groups on the filaments. Thus, the initial microparticle may be formed of substantially uncharged filaments as long as the filaments contain groups that can be modified to form the desired charged group.

Similarly, the charged groups can be introduced by forming the microparticle to include a ligand-specific binding agent, such as lectin, and introducing the complement of the binding agent, e.g., sulfated heparin, into the matrix after particle formation (Tanaka).

The polymer filaments can be constructed and/or modified after particle formation to achieve desired characteristics. For example, when the polymer matrix is to be condensed or decondensed within a desired pH range, the polymer is prepared to include the charged group, e.g., carboxyl group or amine group, whose $pK_a$ is within such pH range.

Similarly, where the polymer matrix is to be used in delivering selected biological or chemical ligand species, preferably charged species, the microparticle is formed to include binding molecules capable of binding the ligand specifically and with high affinity.

D. Microparticle Formation

Several methods are available for forming microparticles having desired sizes in the size range 0.05 and 50 μm, preferably 0.05 to 0.5 μm. These include:

1. Emulsion Polymerization

In this method, monomers are dissolved in a continuous aqueous phase also containing emulsifier micelles plus excess free monomer stored in large droplets in suspension. Polymerization reactions, such as by addition of an initiator molecule or high-energy radiation, leads to polymerization in the regions of the micelles. Phase separation and formation of solid particles can occur before or after termination of the polymerization reaction. Particle size can be controlled by monomer density, micelle density, and polymerization conditions (Kreuter, Cadan, Vanderhoff). As with several of the published methods cited herein for microparticle preparation, it will be appreciated that the published method may need to be modified to include a desired percentage of charged monomers, as discussed above.

2. Emulsion Polymerization in Continuous Organic Phase

In this method, water-soluble monomers are added to a water-in-oil emulsion stabilized by a surfactant, under conditions that polymerization is initiated in the aqueous phase droplets (Kreuter).

3. Precipitation Polymerization

Precipitation polymerization involves polymerization starting from a monomer solution in which the polymer (or microparticle) is insoluble (Kawaguchi, 1991, 1992, 1993, Pelton, 1986, 1988, Tai). Typically in this method, polymerization of monomers in solution is allowed to proceed until desired size polymer filaments are formed, usually under conditions of vigorous mixing.

This method (following Kawaguchi) was followed in preparing synthetic microparticles described in several drug-loading and condensation studies reported below, where the crosslinked polymers described in the reference were prepared to include carboxylated subunits. The basic monomer components used are p-nitrophenol acrylate (NPA), acrylamide (ACm), methacrylic acid (MAc) and methylenebisacrylamine (MBAAm). The purpose of the NPA is to produce reactive nanoparticles, by virtue of the free nitophenol group, and particles can also be prepared without this component.

The components are dissolved in ethanol, at a ratio/amount of MAc/AAm/NPA/MBAAc 10/20/10/5 mmoles in 40 ml ethanol. After bubbling the monomer solution with nitrogen, azobis-isobutyrylnitrile (AIBN) as initiator is added to the monomer solution in an amount between 0.1 to 1.5 g. A large amount of initiator is necessary to achieve high conversion. The flask is placed in a water bath (60° C.) and swirled for up to 24 hours. Conversion of monomer to polymer is monitored, e.g., by gas chromatography analysis of remaining monomer. The size and shape of the resulting nanospheres can be determined by electron or optical microscopy. The hydrodynamic size is measured by photon correlation spectroscopy.

In a related embodiment, particles are formed with the components methacrylic acid (10 mmol)/nitrophenyl acrylate (10 mmol)/methylene bis acrylamide (5 mmol)/ethanol (35 g), employing 0.75 g initiator AIBN, carrying out the reaction at 60° C. for 22 hours under nitrogen. The particle may be treated by reaction with ethylene diamine 100 eq/1 eq particle at room temperature for 48 hours.

4. Encapsulated Polymer Method

In this method, a polyanionic, hydrophilic polymer is crosslinked in an encapsulated form, followed by removal of the encapsulating membrane to leave crosslinked, decondensed particles of a desired final size. The method is illustrated in FIGS. 4A–4D for the preparation of particles using encapsulating lipid vesicle membranes.

Figure 4A:
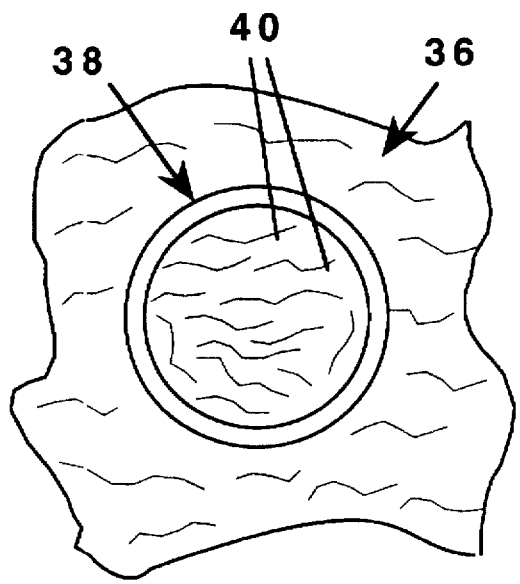
FIGS. 4A–4D illustrate steps in forming polymer-matrix microparticles by lipid encapsulation.

Initially, and with reference to FIG. 4A, an aqueous solution or suspension of the polymer and cross-linking agent (aqueous polymer medium) is encapsulated in lipid bilayer vesicles. A variety of vesicle-forming methods, such as lipid hydration, reverse-phase evaporation, solvent injection, and freeze-thaw methods are available for encapsulating aqueous material in lipid vesicles.

In a preferred method, the aqueous polymer medium is used to hydrate a dried lipid film formed of vesicle-forming lipids, such as a mixture of phosphatidylcholine (lecithin) and cholesterol. The hydration is carried out under mild agitation, to form liposomes with heterogeneous sizes between about 0.05 and 20 microns. The suspension, indicated at 36 FIG. 4A, contains liposomes, such as liposome 38 with encapsulated polymers, such as polymers 40, as well as polymers in the bulk phase of the suspension, as shown.

Figure 4B:
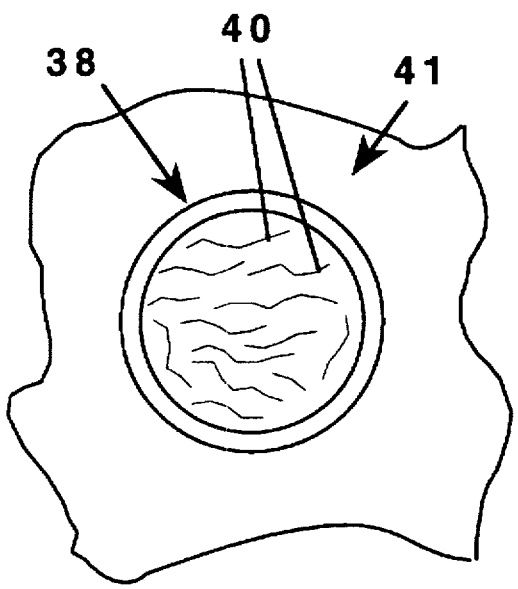

The liposome suspension may be sized, as by extrusion through a polycarbonate membrane or the like to reduce the largest liposomes to a desired upper size, e.g., 2–5 microns. Following this, the suspension may be further size fractionated, for example, by molecular sieve chromatography, to remove liposomes below a selected size range, e.g., 0.5 microns. At the same time, or in a separate step, the liposomes are separated from bulk-phase polymer material, to produce a suspension 41 of liposomes in a polymer-free aqueous medium, as shown in FIG. 4B.

Figure 4D:
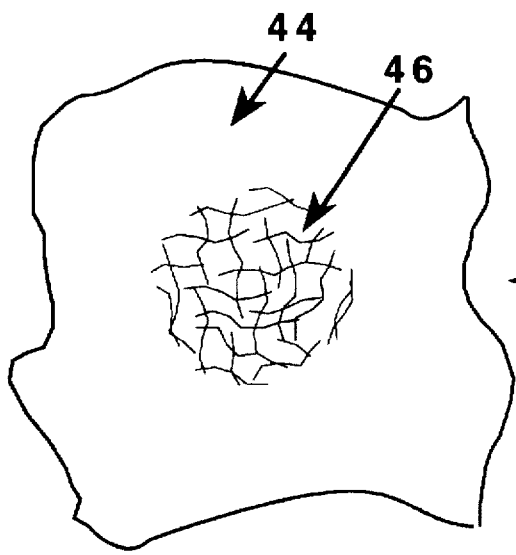
Figure 4C:
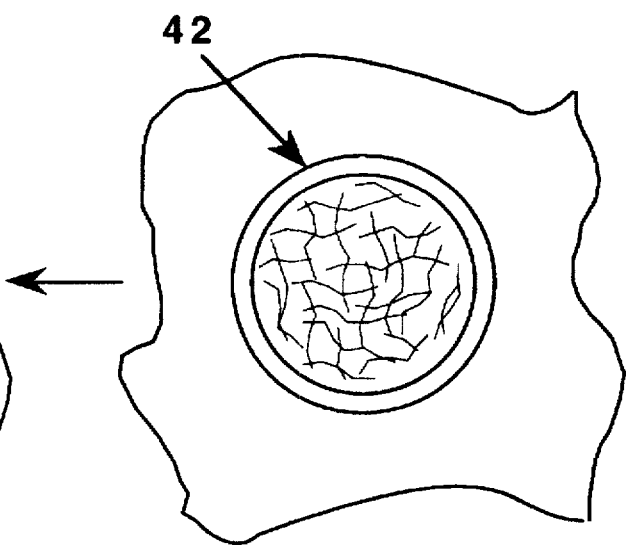

The liposome suspension is now subject to heat or irradiation treatment to initiate crosslinking of the encapsulated polymer suspension, as shown in FIG. 4C, according to standard methods such as outlined above. The cross-linked matrices, such as matrix 42, have the approximate sizes of the encapsulating liposomes.

In the final step, shown in FIG. 4D, the suspension is treated to remove the encapsulating liposome membranes, leaving a suspension 44 of the crosslinked particles, such as particle 46. Membrane dissolution may be produced by detergents, organic solvents, or the like. The microparticles may be separated from the lipid and lipid-solvent components by filtration or the like, then resuspended in an aqueous medium for further processing.

5. Gelatin Dispersion

This is a specific embodiment of a more general approach in which the polymer filaments or monomer subunits used in forming the microparticles are mixed with a suspension of proteins, such as agar, gelatin, or albumin (Kreuter, Tanaka). One method employs alginate plus $Ca^{+2}$ in producing the particles. The mixture is then dispersed under conditions effective to produce desired sized particles containing the mixture components. In the case of gelatin containing particles, the mixture may be cooled during the dispersion process to produce gelled particles having a desired size. The particles are then treated under polymerization and/or crosslinking conditions, preferably under conditions that do not also lead to crosslinking of gelatin molecules to the polymer structure. After microparticle formation, the gelatin molecules may be removed from the structure, with such in a decondensed form, e.g., by heating the material or enzymatic digestion.

Other methods for forming microparticles have been reported, and are contemplated herein for use in preparing charged-polymer microparticles having the properties and characteristics discussed above.

Polymer-matrix microparticles having the rapid condensation/decondensation properties described above can also be made synthetically by a variety of methods. The microparticles are made by forming cross-linking polyionic hydrophilic polymers under conditions which lead to crosslinked matrices in the 0.05 to 50 µm, preferably 0.05 to 5 µm particle-size range, when the particles are in their condensed states.

III. Condensed-Phase Microparticles for Compound Storage

In one aspect, the invention includes a method of storing a compound, typically unstable hydrophilic compound, but also including stable and/or hydrophobic compounds, as discussed below. The method includes infusing the compound into polymer microparticles of the type described above, with such in a decondensed phase, and after compound infusion into the open particle matrices, adding multivalent counterions to the medium under conditions effective to fully condense the microparticles.

When the microparticle formed in accordance with the above methods is suspended in a decondensing aqueous medium, typically one containing a 10–200 mM concentration of monovalent counterions, it is fully hydrated and has a size that is typically 3–4 times larger than the desired condensed-phase particles.

With addition of a multivalent counterion, such as $Ca^{+2}$ or histamine in the case of a polyanionic polymer matrix, the particle will be forced into a condensed phase.

In their condensed phase, the microparticles are substantially dehydrated, and have a water content that is less than about 30 percent, preferably less than about 5–15 percent by volume of water.

To determine the approximate water content of the microparticles in their condensed phase, the size of the particles can be compared before and after complete hydration, e.g., by suspending the particles in 100% ethanol. Particles which by this criterion typically contain less than about 30% by volume, preferably less than about 5–15% by volume of entrapped water, are suited for use in the method.

In practicing the method, particles prepared and selected as above are suspended in an aqueous decondensing medium in the presence of the hydrophilic compound to be stored. The compound is typically one which cannot be stored or is difficult to store either in solution or in a dehydrated form. The compound may be difficult to store either because it loses its activity, or forms undesired side products, or tends to aggregate or otherwise loses its solute properties when stored in an aqueous medium or when dehydrated, e.g., by lyophilization.

One general class of compounds suitable for use in the method are small, water soluble drug molecules, as exemplified by aminoglycoside antibiotics, such as doxorubicin or daunorubicin. The aminoglycoside compounds tend to promote, and in turn undergo, free radical reactions that lead to a loss of activity and/or appearance of more toxic side products. Other small drug compounds, particularly those capable of chelating iron or other metals, those capable of absorbing visible light, and those capable of acting as substrates for contaminating enzymes, such as esterase, may also show instability on storage in solution and/or in a dehydrated form.

A second general class of compounds suitable for use in the invention are polypeptides, including both peptides and proteins, such as peptide hormones, e.g., insulin, cytokines, and a large number of enzymes. Peptides or proteins may be unstable due to aggregation on storage or on drying, denaturation on freezing or drying, dissociation into inactive subunits, proteolysis in solution, free-radical or oxidative damage that occurs on storage, progressive inactivation in the absence of critical factors or co-factors, or intermolecular crosslinking or polymerization.

Still another general class of compounds suitable for the invention are the water soluble vitamins, such as flavin-containing vitamins and ascorbate.

Other general classes of water-soluble compounds that are difficult to store in solution or on dehydration, such as free-radical initiators, dyes, and unstable water-soluble organic compounds are also contemplated.

The compounds are preferably ionized or ionizable at a selected pH, and have a net charge in an ionized form which is opposite to that of the charged groups on the matrix filaments. In the case of a particle matrix formed of polyanionic filaments, the compounds have charged or ionizable amine groups that provide a positive charge to the compound at a selected pH, preferably between pH 6–10. Where the compound is a polypeptide, the number of positively charged amine groups should be in substantial excess of the number of negatively charged carboxyl groups.

Similarly, where the compound has a negative charge at a selective pH, such as ascorbate, or negatively charged polypeptides, the microparticle matrix is formed of polycationic filaments.

To prepare the condensed-phase microparticles, the compound to be stored is mixed in an aqueous medium with a suspension of microparticles in a decondensed phase. The concentration of compound in the suspension is typically between about 0.05 and 10 mM. The concentration of microparticles is preferably such as to allow substantially complete saturation of the matrix charge groups by the charged compound. This should occur at an effective compound concentration of up to 100–500 mM or greater for small drug molecules, and at a proportionately smaller concentration for multivalent species, such as polypeptides.

The ionic composition of the medium is such as to retain the microparticles in a decondensed condition, preferably including a low concentration of monovalent counterions, e.g., 10–200 $Na^+$. The pH of the medium is preferably between the $pK_a$ of the matrix polymer filament charge groups and the $pK_a$ of the compound charge group(s), insuring that both groups will be charged and capable of forming electrostatic bonds with one another.

The mixture is allowed to incubate, e.g., at room temperature, until the matrix has become fully saturated with the compound. The kinetics of compound uptake into the drug may be followed by a variety of standard methods, e.g., by removing aliquots of suspension at periodic intervals, condensing the particles, washing the particles to remove non-entrapped drug, and assaying the condensed particles for the presence of entrapped compound.

After a desired loading level is reached, preferably at or near saturation, the matrix is condensed by addition of multivalent cations, such as $Ca^{+2}$ and/or histamine. The final concentration of condensing counterion is preferably between 5–100 mM.

Figure 5:
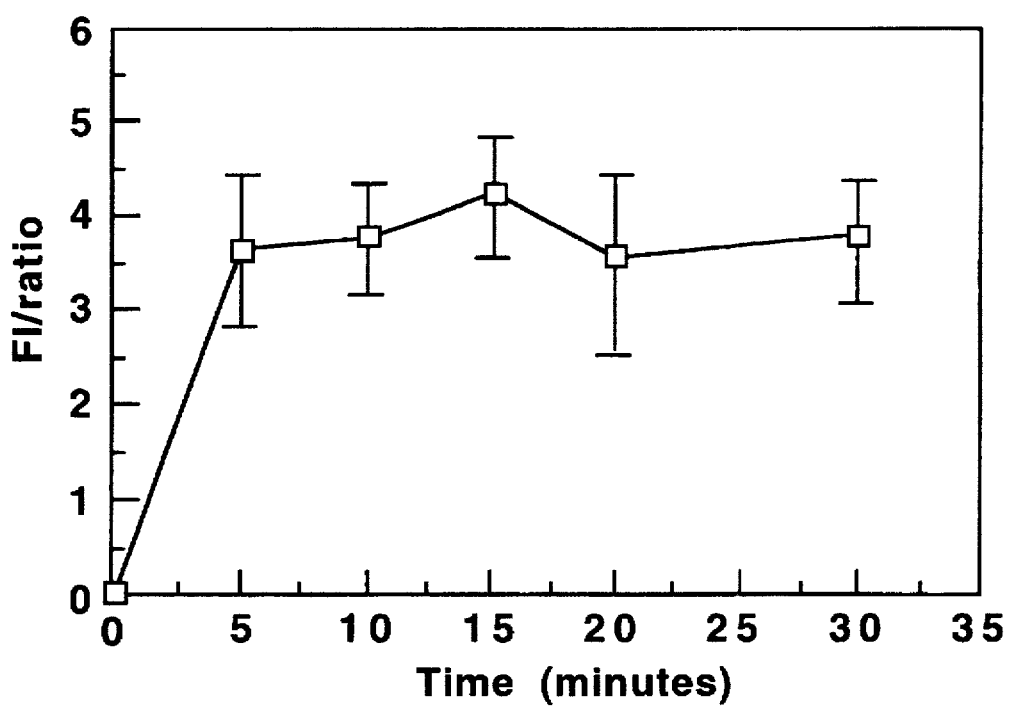
FIG. 5 shows a plot of doxorubicin loading into decondensed microparticles.

FIG. 5 shows a plot of uptake of doxorubicin into crosslinked heparin microparticles, such as isolated in accordance with Example I. At an compound concentration of 0.5 mM, compound loading to a final effective concentration of about 200 mM was achieved after 30 minutes. At a compound concentration of 0.1 mM, loading to the same level was achieved after about 45 minutes. Similar results were obtained with synthetic microparticles.

As seen from the above, the charged drug compound partitions into the microparticles with a partition coefficient, with respect to the aqueous medium, of over 1,000. Thus, according to one advantage, the method of the invention provides a compound-concentrating effect for loading high levels of compound into the particles from a low aqueous loading concentration.

The effective concentration of compound in the loaded microparticles may be several times greater than the maximum solubility of compound in the aqueous loading medium. This is true particularly in the case of a compound with lipophilic character, since the condensed phase matrix will provide a low-hydration environment.

Figure 6A:
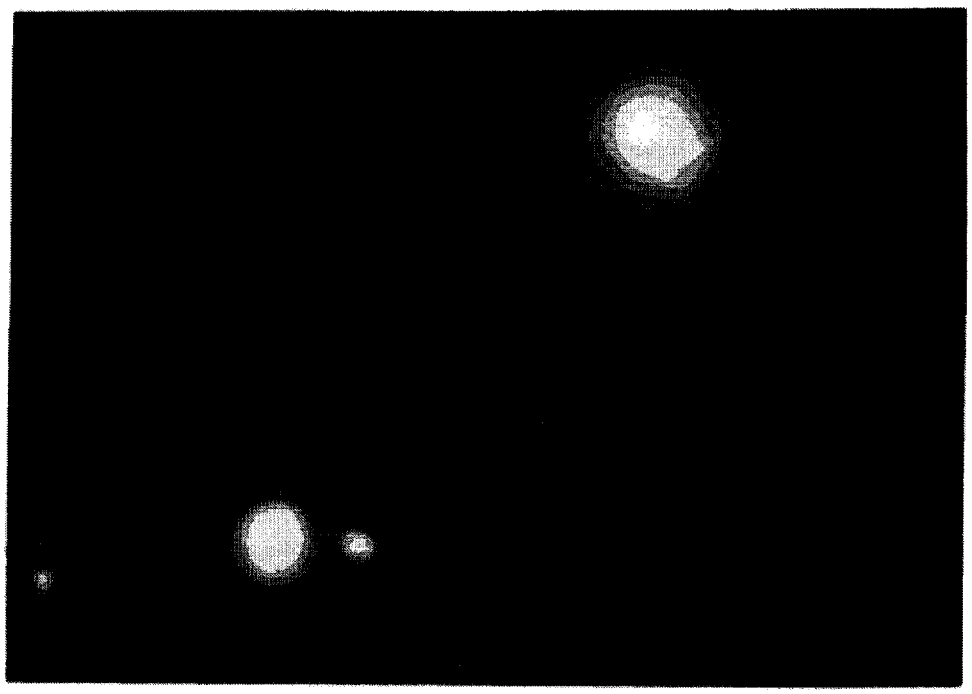
FIGS. 6A and 6B are photomicrographs of a condensed-phase mast-cell (6A) and synthetic (6B) microparticles loaded with doxorubicin.
Figure 6B:
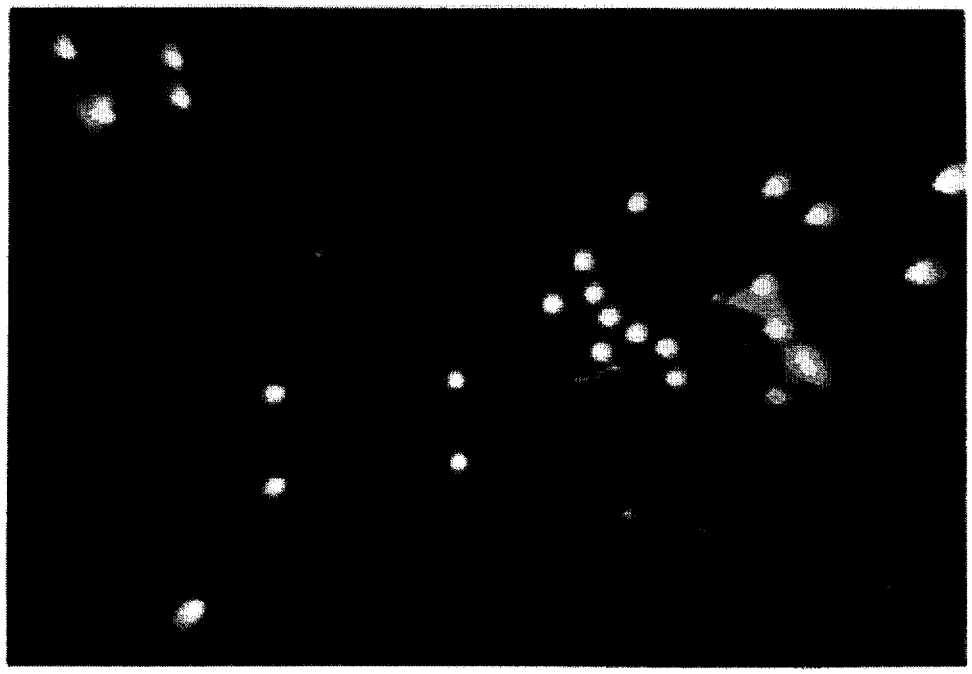

FIGS. 6A and 6B show heparin cross-linked microparticles from mast cells and synthetic microparticles, respectively, after loading with doxorubicin. The size of the condensed polymers is about 3 μm for the heparin matrix particle, and about 2 μm for the synthetic polymer. Typically, the particles in the condensed state have volumes which are about ⅕–⅓ those of the decondensed particles, and have a water content between about 5–30% by volume of the particle. As indicated above, the residual water volume of the condensed-phase particles can be estimated from the reduction in size or weight after dehydration, e.g., by ethanol extraction.

In another embodiment, the compound to be stored is itself a multivalent counterion capable of condensing the matrix. Histamine is example of a small drug compound of this type. Small cationic or anionic polypeptides are other examples of compounds that are desired to be stored, and which also serve as condensing agents. FIGS. 8A, 8C, 8E, and 8G show light photomicrographs and fluorescent photomicrographs (8B, 8D, 8F, and 8G) microparticles treated under various condensation and decondensation conditions. In 8A and 8B, microparticles (prepared as in Example 1) were suspended in an aqueous medium, pH 3.5, under conditions of decondensation. The particles were then loaded with fluorescent-labeled histamine, 150 mM in the aqueous medium, causing condensation of the particles (8C). The fluorescent label in the condensed-phase particles observed on condensation was retained in a probe-free solution (8D) indicating that the entrapped histamine was not freely diffusible.

When the condensed-phase microparticle from above were suspended in a $Na^+$-containing medium, the particles quickly decondensed (8E) and the entrapped fluorescent label quickly diffused away (8F). A new cycle of condensation, this time by unlabeled histamine caused particle condensation (8G), but failed to increase fluorescence in the condensed-phase particles (8H), confirming that labeled histamine was indeed released from the particles after decondensation.

After particle condensation, the particles may be further processed to achieve desired solubility properties and storage conditions. Since the condensed-phase particles have excluded much of the water of hydration, the condensed particles may be treated at this stage to increase their surface hydrophilicity. For example, the particle surfaces can be chemically derivatized with hydrophilic moieties, such as short hydrophilic polymer chains, according to known chemical derivatization methods. More simply, the condensed-phase particles can be incubated with a surfactant, such as a bile salt or fatty-acyl-PEG or cholesterol-PEG surfactant, under conditions effective to cause partitioning of the surfactant into the outer surface of the microparticle, with the hydrophilic moiety of the surfactant being exposed to aqueous medium. Surfactants of this type, having PEG chains in the 1,000–5,000 dalton range are commercially available. The PEG coating may serve the additional function, in a parenteral therapeutic composition, of extending the blood circulation time of the PEG-coated, condensed-phase particles.

Alternatively, a coat of hydrophilic material, such as polylysine or other polypeptide can be formed on the condensed particles. One method for forming a protein polyvalent peptide coat on a condensed microparticle is described in Section IV.

Finally, in preparing the particle for storage, the composition may be washed for storage in an aqueous condensing medium, filtered or centrifuged to remove aqueous suspension medium, for storage in a condensed, partially hydrated form, or dehydrated, e.g., by lyophilization, for storage in a dried form. In another embodiment, the condensed-phase particles may be stored in an aqueous medium, preferably after washing the particles to remove the aqueous loading medium.

According to another important aspect of the invention, it has been discovered that the particles remain in a highly condensed form in aqueous suspension, showing little or no compound leakage from the condensed-phase particles, even after an extended storage period.

FIG. 7A shows a plot of doxorubicin release rate from condensed-phase microparticles stored in distilled water. As seen, the half-life of drug release from the particles is about 1 hour, even though the distilled water medium is itself incapable of causing condensation of decondensed particles. The study illustrates the limited degree of diffusion of counterion and drug from the condensed-phase particles. When the particles are stored in partially dried form, or in an aqueous medium with condensing counterions, the particles may be stored without appreciable leakage over several weeks to months.

When the condensed-phase particles are suspended in 150 mM $Na^+$, i.e., decondensing conditions, the drug is rapidly released from the particles (FIG. 7B).

A composition containing the condensed-phase particles with entrapped compound is useful in therapeutic applications, as drug-delivery particles for parenteral, oral, or topical drug delivery. In parenteral use, the condensed-phase particles have the advantage first that a high concentration of water-soluble drug can be administered without severe osmotic effects at the site of administration, since the condensed-phase particles are essentially nonosmotic until they decondense and release drug.

Secondly, the compound can be stored, either in dry-particle or suspension form, with little loss of activity over an extended storage period. This feature is advantageous particularly for a variety of polypeptide which may otherwise be unstable on long-tern storage.

Figure 9:
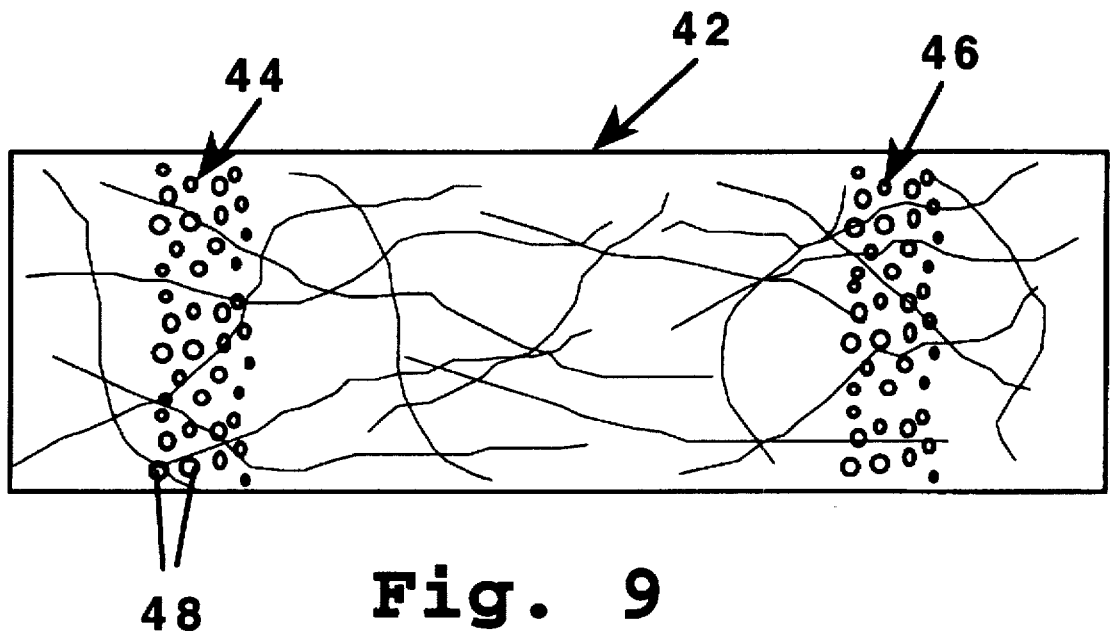
FIG. 9 shows a diagnostic device employing a condensed phase microparticle prepared in accordance with the invention.

The particles are also useful in diagnostic applications, both as a stable storage form of a diagnostic reagent, and as a means for providing rapid release of reagents under selected reaction conditions. FIG. 9 shows a dry diagnostic test strip 42 composed of a fiber mesh, and containing first and second compositions 44, 46 of dried (partially hydrated) condensed-phase particles, such as particles 48 in composition 44, constructed in accordance with the invention. The particles are immobilized in the mesh fibers as indicated.

The first composition contains a first assay reagent which is released into the strip on contact with a fluid sample, which contains a high concentration of monovalent ions. The first reagent may be, for example, an antibody capable of reacting with the analyte of interest, or an enzyme capable of acting on the analyte to produce an analyte-specific reaction product.

After reaction of the sample fluid with the first reagent, migration of the sample along the strip leads to release of a second reagent, producing a second reaction that is diagnostic for the presence of the analyte or analyte-derived molecules. The second reagent may be, for example, a dye or other reporter reagent.

One advantages of the condensed-phase particle composition in this application is the stable storage of reagent compound, such as enzymes, antibodies, and dyes in a diagnostics kit. Another advantage is the rapid release of entrapped compound on contact with aqueous medium or by other activating means, such as introduction of monovalent counterions. This is in contrast to the relatively slow release of particles in crystallized or aggregated form.

The composition is also useful as a delivery vehicle for reagents in chemical or biochemical reactions, where the reagent is unstable on storage, or where it is desirable to introduce the reagent at a selected step in a reaction, e.g., by decondensing the particles with a monovalent counterion.

IV. Delayed Release Particle Composition

In another aspect, the invention includes a compound-release composition formed of a suspension of microparticles having average sizes in a selected size range between 0.05 and 50 μm, preferably 0.5 to 5.0 μm. For use in parenteral drug delivery, the microparticles preferably have sizes between 0.05 to 0.5 μm.

Each microparticle is composed of a condensed-phase matrix of crosslinked polyionic polymer filaments capable of expanding to a decondensed phase in the presence of monovalent counterions. The matrix contains entrapped small molecules, such as therapeutic or reagent molecules, and polyvalent counterions, preferably polyvalent polymer molecules, effective to delay the release of the small molecules from the microparticles, when the microparticles are exposed to monovalent counterions.

In a related aspect, the invention includes a method of delaying the release of small molecules entrapped in a condensed-phase polyionic microparticles of the type described above, by condensing the microparticles, either partially of completely, with polyvalent counterions selected to produce a desired rate of particle decondensation in the presence of monovalent counterion.

In one general embodiment, described in Section A, the polyvalent counterion is relatively small and capable of readily diffusing throughout the matrix, acting as the sole condensing agent. In a second general embodiment, described in Section B, the polyvalent counterion is poorly diffused into matrix, by virtue of its size or solubility properties, and is taken up in an outer shell region of the matrix only, with complete particle condensation occurring by a small multivalent counterion, such as $Ca^{+2}$.

A. Delayed Release Microparticles

Figures 10A, 10B:
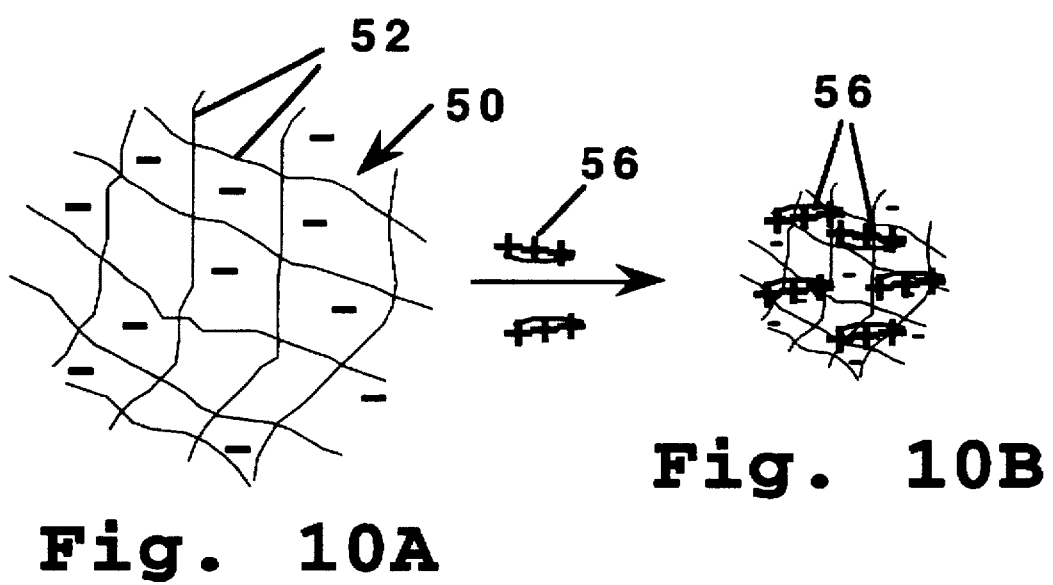
FIGS. 10A and 10B illustrate steps in preparing a condensed phase microparticle in a compound-release composition constructed in accordance with another embodiment of the invention.

FIG. 10A illustrates a decondensed polyionic matrix 50 of the type described above, in this embodiment, formed of crosslinked polyanionic filaments, such as filaments, 52. The matrix is preferably infused with a small compound (not shown) which is to be delivered from the particle. Compounds which are suitable for entrapment in condensed-phase microparticles are discussed above.

The particles with infused compound are condensed with a polyvalent counterion capable of diffusing through the matrix, with such in its decondensed form. In FIGS. 10A and 10B, the condensing agent is a trivalent counterion indicated at 56. The condensing agent produces a condensed-phase particle, such as indicated at 58, with the condensing agent and entrapped small molecule distributed throughout the matrix, as indicated. An example of such a condensing agent is the peptide mastoparan, a 14-amino acid peptide having three positively charged groups. Other polycationic polymers, including other polypeptides with multiple lysine groups, or polyamine polymers, including polyquaternary amines, are also suitable. The sizes of the polyvalent species is preferably less than about 5–10 Kdaltons, and preferably has no more than about 5–10 charged groups/molecule.

The concentration of polyvalent condensing agent needed to produce full particle condensation may be substantially lower, with respect to the concentration of monovalent counterions, than is required for particle condensation with a divalent counterion, such as $Ca^{+2}$ or histamine. For example, 1 mM mastoparan is effective to produce complete condensation of particles in the presence of 150 mM Na salt. In general, the higher the valency, the more strongly the condensing agent can be expected to displace monovalent counterions in the matrix, and the lower the ratio of polyvalent/monovalent counterions that will be required for achieving particle condensation.

The particles are incubated with the condensing agent until complete particle condensation has occurred. As above, the degree of condensation may be monitored observing changes in size and or amount of residual water present. The time required for condensation may be on the order of several minutes or more, and will generally depend on the size of the polyvalent species, and the size of the condensed-phase microparticles.

After complete condensation, the particles may be further processed, as above, by washing and/or storage in a dried state.

According to an important feature, the polyvalent species used to condense the particles can be selected to control the rate of particle decondensation when the condensed-phase particles are exposed to monovalent counterions. As indicated above, polyvalent counterions having high valency, e.g., 5–10 charged group per molecule, give slower decondensation times than lower-valency counterions, e.g., 3–5 charged groups. Microparticles (2–3 μm) condensed with mastoparan (a trivalent species) showed decondensation times of about 15–20 minutes when exposed to medium containing about 150 mM $Na^+$. This contrasts with the rapid decondensation (e.g., 2–30 secs) that occurs in 2–3 μm size condensed-phase microparticles condensed with divalent counterions.

For therapeutic applications, the composition is prepared to achieve a desired rate of decondensation and drug release in a physiological medium, such as the upper gastrointestinal tract or bloodstream. This may be done by increasing the valency of the counterion until a desired swelling rate in vitro is observed in a selected swelling medium. As in the mastoparan example, the condensing agent itself, e.g., a charged polypeptide, may be the therapeutic molecule itself.

B. Charge-Coated Microparticles

Figure 11A:
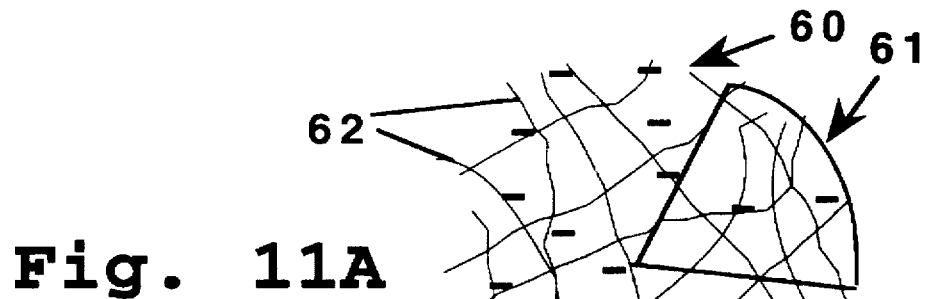
FIGS. 11A–11C illustrate steps in preparing a condensed phase microparticle in a compound-release composition constructed in accordance with one embodiment of the invention.
Figure 11B:
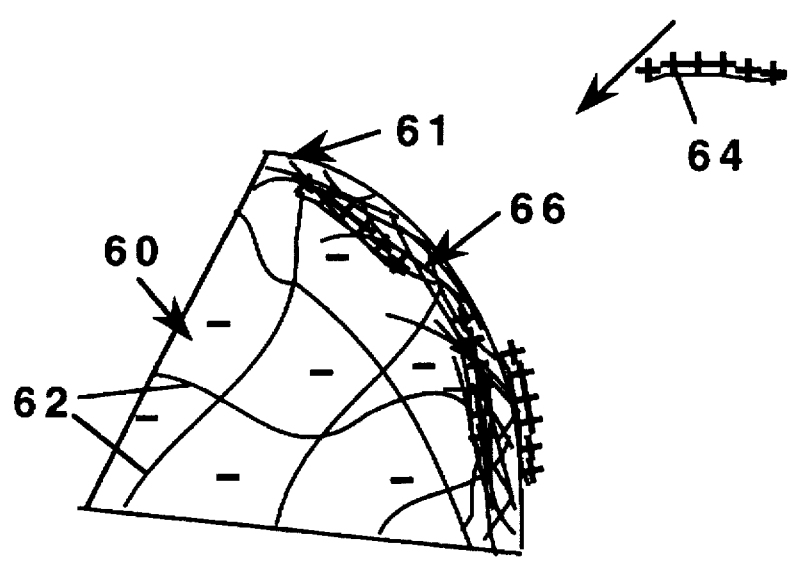
Figure 11C:
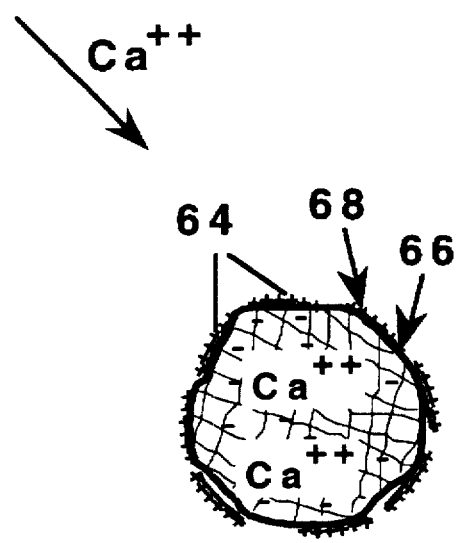

In another embodiment, illustrated in FIGS. 11A–11C, the microparticles are condensed under conditions effective to include the polyvalent species in an outer surface region only of the condensed microparticles.

FIG. 11A illustrates a decondensed polyionic matrix 60 of the type described above, in this embodiment, formed of crosslinked polyanionic filaments, such as filaments, 62. The matrix is preferably infused with a small compound (not shown) which is to be delivered from the particle. Compounds which are suitable for entrapment in condensed-phase microparticles are discussed above. The sector 61 in FIG. 11A is shown in enlarged view in FIG. 11B.

In this embodiment, particle condensation involves two condensing agent. The first agent, illustrated in FIG. 11B, is a relatively large polyvalent species, such as polypeptides or other charged polymers, and indicated here at 64. This agent is effective to penetrate into the outer region of the matrix only.

The effect of the first condensing agent is to partially condense an outer surface region 66 of the matrix which now contains bound polyvalent molecules. The second condensing agent is one capable of readily diffusing into condensing the entire matrix. This agent may be a divalent or polyvalent counterion species of the type discussed above. The second condensing agent is effective to form condensed microparticles, such as microparticle 68 in FIG. 11C, having a surface coating 66 of the polyvalent molecules 64, and small molecules (not shown), such as therapeutic molecules, entrapped in the matrix.

In the embodiment just described, the condensed-phase particle was formed by addition first of the large polyvalent species, and subsequent condensation with a small counterion. The two condensation steps may be carried out together, or in reverse order. To illustrate the latter approach, the particles may be first condensed with a small polyvalent counterion which leads to slow decondensation, then partially decondensed in a monovalent counterion, and finally fully recondensed by addition of the large polyvalent species. The latter approach has the advantage of forming a more dense packing of polyvalent species in the outer surface region of the microparticles, for achieving slow rates of decondensation.

As above, the polyvalent agent used to condense the outer surface region of the polymer may itself be a therapeutic molecule, such as a charged polypeptide.

The method just described may also be employed in forming condensed-state microparticles having a desired surface coating. This method is illustrated in FIGS. 12A and 12B. Here it is desired to coat the microparticles with polyethyleneglycol (PEG) polymer strands to achieve enhanced circulation time of the microparticles in the bloodstream. In the method, a decondensed matrix, such as shown at 70 in FIG. 12A is incubated with a large polyvalent molecule 72, such as a positively charged polypeptide, that has been derivatized with PEG chains, such as indicated at 74. Addition of a small condensing agent, such as $Ca^{+2}$, either before, during, or following the surface coating step, as discussed above, produces a condensed-phase microparticle 78 having a surface coating 76 of the desired polymer.

V. Encapsulated Microparticle Composition

This section describes a particle composition for rapid release of an entrapped compound at a target site, and methods for producing the composition. The suspension is designed to release a particle-entrapped compound when the particles of the composition are exposed to a selected target stimulus related to pH, temperature, or the presence or absence of a selected ligand, such as an antigen or an antibody. According to an important feature of the invention, the target stimulus is effective to trigger rapid release of the compound, by an amplified or cascade ion influx mechanism.

The composition is formed of a suspension of encapsulated microparticles, such as microparticle particle 80 shown in FIG. 13. Each particle includes a polymer-matrix microparticle 82 of the type described above, with such in a condensed phase, and a lipid bilayer membrane 84 encapsulating the microparticle. The compound to be released, such as indicated at 86, is entrapped in the condensed particle matrix. The encapsulated contents of the particle also includes a multivalent counterion at a concentration sufficient to maintain the microparticle in a condensed state. The lipid membrane has a surface coating of anti-ligand molecules, such as molecules 88, as described below.

A. Preparing Encapsulated Microparticles

To prepare the particle composition, polyionic-fiber microparticles of the type described above are prepared or isolated. The sizes of the microparticles, in a condensed state, are preferably in the size range 0.05 to 5µ for preparation of a diagnostic composition and 0.05 to 0.2 µm for a drug-delivery composition. In preparing particles in a decondensed state, the sizes of the particles may be 2-3 times the desired condensed-state size.

Methods of entrapping a selected compound, preferably a water-soluble compound, follow the same methods discussed above in Section III and IV. For use in a drug-delivery composition, the compound may be any therapeutic compound suitable for entrapment in the condensed-phase matrix. Exemplary compounds include anti-tumor compounds, anti-bacterial, anti-viral, or anti-fungal agents, immunosuppressant compounds, and polypeptides, such as enzymes, cytokines, or peptide hormones including water-soluble, amphipathic, or lipophilic drugs. Preferred compounds are those which are ionizable or charged, and carry a charge opposite to that of the matrix polymer filaments, allowing high partitioning of the compound into the matrix, as discussed above.

According to one advantage of the invention, the drug in this mixture may be present in a partially insoluble form, either because the drug is a lipophilic compound having low aqueous solubility, or because the drug, though hydrophilic, is present at a concentration above its normal water solubility.

For preparing particles for use as a diagnostic reagent composition, the compound may be a detectable reporter, such as a colored or fluorescent reporter, or an enzyme, or may include one or more assay reagents, such as ligands, antibodies, enzymes, and/or enzyme substrates.

After mixing the compound(s) to be released and the decondensed particles under conditions effective to infuse the particle matrices with the compound, the particles are transformed to a condensed state by addition of multivalent counterion species, to a concentration sufficient to produce decondensing of the particle matrices. If necessary, e.g., where the concentration of monovalent counterions is relatively high, the particles may be condensed by exchanging divalent for monovalent cations in the mixture, e.g., by molecular sieve chromatography or dialysis. The condensing step serves to trap the matrix-infused drug in the particles.

The suspension of condensed particles is then treated, for example, by washing and centrifugation, to remove non-entrapped compound, and the washed particles are resuspended in aqueous medium containing multivalent counterions for maintaining the particles in their condensed state.

A variety of methods are available for encapsulating the condensed particles in lipid vesicle form (Szoka, 1980). Prior to forming the lipid coat, the condensed-phase particles may be treated, as described in Section III, to produce a hydrophilic coating on the particles.

In one lipid-coating method, liposomes containing a desired lipid composition are sonicated extensively to form small unilamellar vesicles (SUVs), preferably in the 30-70 nm size range, and the SUVs are lyophilized. A concentrated suspension of condensed particles, prepared as above, is added to this lyophilizate, preferably in an amount estimated to provide an encapsulated vesicle volume equal to the total microparticle volume.

After allowing the vesicles to rehydrate in the presence of the particle suspension, the vesicle/particle suspension is subjected to several freeze-thaw cycles, leading to larger uni- and oligolamellar vesicles encapsulating the microparticles. Nonencapsulated particles can be separated, for example, by centrifugation, from encapsulated microparticles. The encapsulated microparticles may be further processed to remove larger-size vesicles, e.g., those larger than 0.2–0.4µ, or to reduce vesicle size by standard membrane extrusion methods (Szoka, 1978).

Another method for encapsulating particles involves a reverse phase evaporation method of liposome formation (Szoka, 1980). To modify the method to the needs of the present invention, a concentrated aqueous microparticle suspension containing entrapped compound is emulsified in a solution of phospholipids in a lipophilic solvent, such as chloroform. The emulsion that forms is a water-in-oil emulsion made up of individual microparticles, each coated by a phospholipid monolayer. The emulsion is reduced to an unstable lipid gel by solvent removal.

With mechanical agitation, either with or without the addition of additional aqueous medium, the gel collapses to form oligolamellar vesicles with encapsulated microparticles. Further treatment may involve liposomes sizing, as by extrusion through a defined-pore size polycarbonate membrane, and removal of nonencapsulated particles.

In a third general method, the condensed microparticles are suspended with membrane-forming lipids in an aqueous solvent containing a bile salt, alcohol, or other solvent components capable of destabilizing vesicle membranes. The mixture of lipids and particles is then treated, e.g., by dialysis, effective to remove the destabilizing solvent component, until stable lipid bilayer membranes form about the condensed particles.

The suspension of encapsulated particles may be further treated, e.g., by centrifugation or molecular sieve chromatography, to remove undesired solvent components or contaminants.

In a related method, the condensed microparticles are mixed with a suspension lipid vesicles, under conditions that promote lipid exchange between the vesicles and particles. Typically, the mixing is carried out above the phase-transition temperature of the lipids. The reaction is continued until lipid bilayers have formed about the particles.

As above, the vesicles may be further processed to obtain desired sizes less than about 0.5µ, and to remove non-encapsulated microparticles.

B. Vesicle Membrane Properties

The encapsulated microparticles constructed in accordance with the invention are designed to allow localized vesicle lysis and counterion exchange across the vesicle membrane under selected target conditions. Various modifications of the encapsulating lipids can be made, to provide selective lysis of or exchange across the vesicle membrane, as exemplified below.

1. Attachment of Anti-Ligand Molecules to the Vesicle Membrane

In the embodiment of the invention illustrated in FIG. 13, the microparticles have surface-attached anti-ligand molecules, such as antibodies 88, that are part of a ligand-anti-ligand pair, where the antibody in the pair may include a ligand-specific antibody fragment, such as an $F_{ab}$ fragment. Methods for coupling anti-ligand molecules to lipid bilayer surface groups are well known. Typically, the bilayer membranes are formulated to include lipids, such as phosphatidylcholine (PE), phosphatidylserine (PS), or phosphatidylinositol (PI) with reactive polar-head groups, such as amine, hydroxyl, or sugar groups, respectively. In one general approach, the anti-ligand molecules are activated, such as by reaction with N-hydroxysuccinamide (NHS) or other activating agent, then reacted with the particles, to covalently link the anti-ligand molecules to the outer-surface lipid groups.

In another general embodiment, the anti-ligand molecules are joined to the lipid membrane by reacting the particles with the anti-ligand in the presence of a condensing agent, such as dicyclocarbodiimide, or a suitable bifunctional reagent.

Alternatively, the anti-ligand may be initially conjugated to a lipid component, such as a phospholipid, and this lipid then used in preparing lipid-encapsulated particles. The anti-ligand in this embodiment is contained on both sides of the lipid bilayers in the encapsulated particles.

2. Incorporation of Ion-Selective Channels into the Vesicle Lipid Membrane

In another embodiment, the trigger mechanism in the lipid bilayer, for responding to an external stimulus, is an ion-selective channel. Typically, the ion channels are selective for monovalent cations, such as sodium or potassium ions. Such channels are formed by a single large polypeptide or a multimer of polypeptide subunits that traverse the cell membrane. The multimers may be formed of the same subunit or different subunits. An example of a channel that is formed by a single polypeptide is the calcium-activated potassium channel from renal medullary cells, described in greater detail below. The nicotinic acetylcholine illustrates a channel that is formed from different subunit types.

A number of sodium and potassium ion channels have now been characterized, cloned and purified from a diversity of cell types and life forms (C.f., Hucho, 1993). Such channel-forming polypeptides or proteins can be purified or cloned and purified according to methods known in the art, and incorporated into liposomes, as discussed Part A above.

By way of example, the renal medullary calcium-activated potassium channel is isolated from renal medullary membranes after solubilization using a common biological detergent (CHAPS). Functional reconstitution of the channels into membranes can be achieved by mixing a solution of the detergent-solubilized channels with a sonicated soybean lipid-detergent solution, and applying the mixture to a small gel filtration column (Sephadex G-50) (Klaerke, 1987). The resulting channel-containing vesicle population is then used to coat microparticles, according to one or more of the general methods described in Part B, above.

The ion channels present in the encapsulating membrane bilayer are initially present in a closed state and are activated to open by a specific stimulus. The particular stimulus required to effect channel opening depends on the channel type present in the membrane. Stimuli for opening include channel-specific ligands, a voltage potential across the membrane, or a high concentration of an ion, e.g., calcium ion, as discussed below.

Figure 16A:
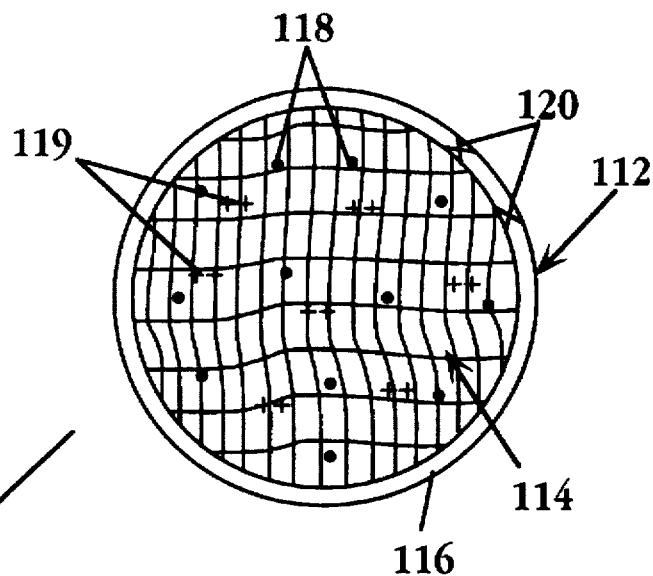
FIGS. 16A–16C illustrate an encapsulated microparticle (FIG. 16A) having monovalent ion channels present in the vesicular membrane, with stimulation of such channels to open (FIG. 16B) resulting in passage of monovalent ions from the external medium into the microparticle, and rapid decondensing of the microparticle's polymer matrix to release entrapped drug into the interior of the cell (FIG. 16C)
Figure 16B:
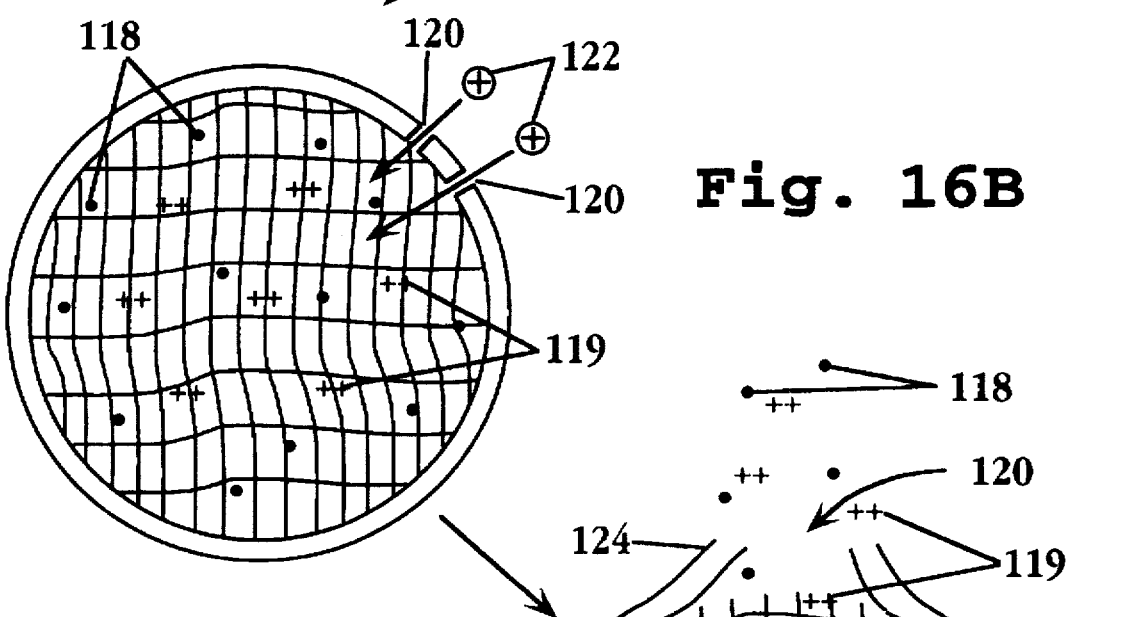
Figure 16C:
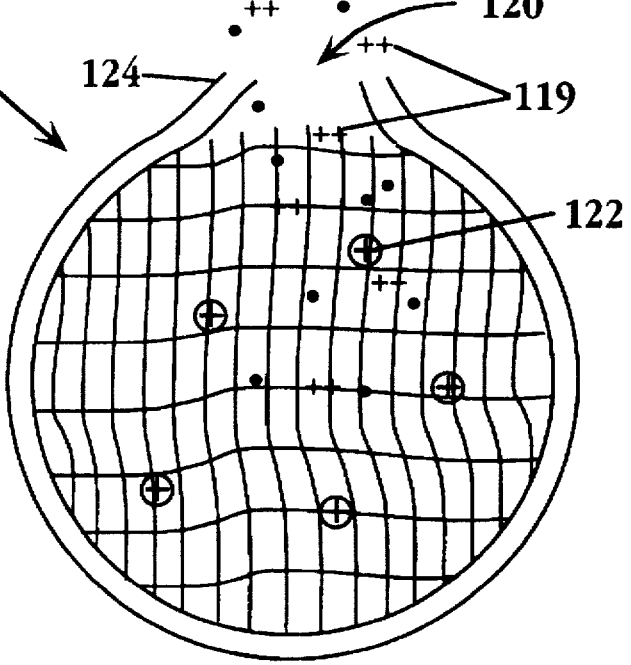

FIG. 16 shows an ion channel-containing encapsulated microparticle 112, including a matrix microparticle 114 in a condensed phase, as described above, and a lipid bilayer membrane 116 encapsulating the microparticle. A compound to be released, indicated at 118, is entrapped in the condensed particle matrix. Also present in the matrix is a multivalent counterion 119 at a concentration sufficient to maintain the microparticle in a condensed state. The bilayer includes monovalent-selective ion channels, such as channels 120, spanning the vesicle lipid membrane. Such channels are able to open in response to selected stimuli as illustrated in FIG. 16B, to permit influx of monovalent ions, such as $Na^+$ and/or $K^+$ present in the environment, indicated at 122. Such influx results in localized decondensation of the microparticle in the region of initial influx, causing further perturbation of the membrane and a cascade-like breakdown in the integrity of the bilayer membrane, as indicated in FIG. 16C, with rapid release of drug compound 119 into the surrounding medium, e.g., over a time span of several hundred milliseconds or less.

The particle composition is designed so that membrane triggering occurs at the target site, e.g., at a bloodstream target site, or at a tissue site, such as one involving cell- or tissue-specific surface antigens, or a high local concentration of a particular ligand or ion. Below are discussed several representative ion channels that may be used in the present invention, and the applicable triggering mechanism for each.

One channel protein is the calcium-activated potassium channel isolated from renal medulla. This channel, when reconstituted in liposomes, is stimulated to open by elevated calcium levels in the bathing medium. ($K_{1/2}$ approx.=0.2 micromolar at pH 7.2) When open, the channel selectively permits passage of potassium. Calcium-activated potassium channel opening can be modulated by a variety of extracellular conditions. For example, opening of the channel is inhibited significantly by increasing hydrogen ion concentration (lowering pH), such that at pH less than 5, very little or no channel opening is observed. In addition, channel opening can be modulated by the presence of local anesthetics, such as quinidine. (Klaerke).

Another channel protein is a ligand-gated ion channel. Ligand-gated channels are also classified as receptor molecules that contain or form an intrinsic ion channel. Such channels open when a ligand, such as a neurotransmitter ligand, binds to an extracellular site on the channel. An example of a ligand-gated monovalent ion channel is the glutamate receptor. This receptor forms an internal channel that transports sodium or potassium. There are at least three forms of this channel, each described by its pharmacological specificity: the NMDA channel, the AMPA channel and the kainate channel, and genes have been identified for each (Hucho).

Another type of ligand-activated channel is the nicotinic acetylcholine (Ach) receptor, such as is particularly found on muscle and neuronal cells. Both types of Ach receptor form channels in the membrane that conduct sodium, potassium and, to a lesser degree, calcium, and are activated to open in vivo by the neurotransmitter acetylcholine. These channels differ from the glutamate channel described above, in that they are composed of five subunits. Muscle-derived channels are composed of four different protein subunits of varying sizes that form a pentamer (generally, $\alpha_2\beta\epsilon\delta$, while neuronal channels are formed by a pentamer of $\alpha$ and $\beta$ subunits. Generally, all or substantially all of the subunits are required to reconstitute a functional channel; however, in at least one case (an Ach channel of locust origin), a functional channel has been formed from a single subunit (Hucho).

Yet another stimulus for opening of certain monovalent ion channels is voltage drop across the membrane. A family of voltage-activated potassium channels has been identified, based on sequence homologies of an approximately 500 amino acid polypeptide that contains six transmembrane regions. Members of the MBK/RBK/HBK voltage activated potassium channel are ubiquitous, having been cloned and characterized from a number of sources ranging from Drosophila to human. Channel family members differ broadly in their channel properties, including mean channel open time, conductance and voltage operating ranges, and these differences can be exploited according to the voltage characteristics of the particular target tissue. Use of voltage-sensitive channels in compositions of the invention may be appropriate, when the target region or tissue is one that has an ionic composition or pH that is dramatically altered, in comparison to the blood or interstitial fluid. Thus, compositions are formed that are essentially isoelectric with respect to the blood, then delivered to a region of hyper- or hypotonicity. Such conditions will provide a voltage-drop across the encapsulating membrane effective to cause opening of voltage-activated channels present in the membrane and subsequent influx of sodium or potassium ions from the environment to result in rupture of the membrane and expulsion of microparticle entrapped compound, as discussed above.

3. Selected Lipids

The lipid vesicle membrane can also be composed of lipids whose bilayer phase properties are affected by heat, irradiation, change in local pH conditions, or enzymatic degradation.

Heat-triggerable particles are composed of lipids whose phase transition temperature is above a selected temperature, e.g., normal body temperature. These particles are relatively stable, in terms of membrane leakiness, below the lipid phase transition temperature, but show increased leakiness to ions above the phase transition temperature. Higher phase transition in acyl-chain lipids, e.g., phospholipids, increases with increasing saturation of the acyl chains. Purified phospholipids, such as PC, whose acyl chain composition is such as to give a phase transition temperature of about 37° C. are commercially available.

Some vesicle-forming lipids, such as lysolecithin, are readily degraded by phospholipase enzymes at a selected pH, and can be used in a composition designed for triggering by these enzymes at a target site.

In another embodiment, the lipid-bilayer membranes are constructed to include a plasmalogen lipid having the general formula:

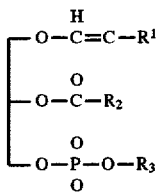

where; $R_1$ and $R_2$ are hydrocarbon chains having lengths from about 10–24 atoms, and which may include unsaturated carbon-carbon bonds, and $R_3$ is a phospholipid phosphate-attached head group, e.g., a serine, choline, ethanolamine, inositol and inositol analogs, or where $R_3$ is absent, giving a double charged phosphate head group. More generally, the plasmalogen is a phospholipid in which at least one of the hydrocarbon chains contains an $\alpha,\beta$-unsaturated ether functional group, such as a vinyl ether, within about 4 to 6 carbons of the charged polar head group. The bilayer membrane preferably includes 10 mole percent or more plasmalogen lipid, preferably 20–70 mole percent.

The unsaturated ether group is cleaved when exposed to an appropriate concentration of reactive oxygen species (ROS) or acid. Such cleavage results in a perturbation of the membrane micellar structure and permits exposure of the microparticle to monovalent ions in the extracellular medium.

Plasmalogens of the general type described by the above formula are also referred to as aldehydogenic lipids. These compounds are generally dialkylglycerols with two long chain alkyl groups, one or both of which are aldehydogenic chains linked to the glycerol backbone as an $\alpha,\beta$-unsaturated ether, generally a vinyl ether. Examples of such compounds include phosphatidal choline and phosphatidal ethanolamine. A particularly useful plasmalogen compound is 1-alk-1'-enyl-2-palmitoyl-sn-glycero-3 phosphocholine. U.S. Pat. No. 5,277,913, incorporated herein by reference, provides methods for producing plasmalogen lipids and for incorporating such lipids into liposomes. These methods are adaptable to the methods described in Section V.A. herein for producing encapsulated microparticles.

Figure 17A:
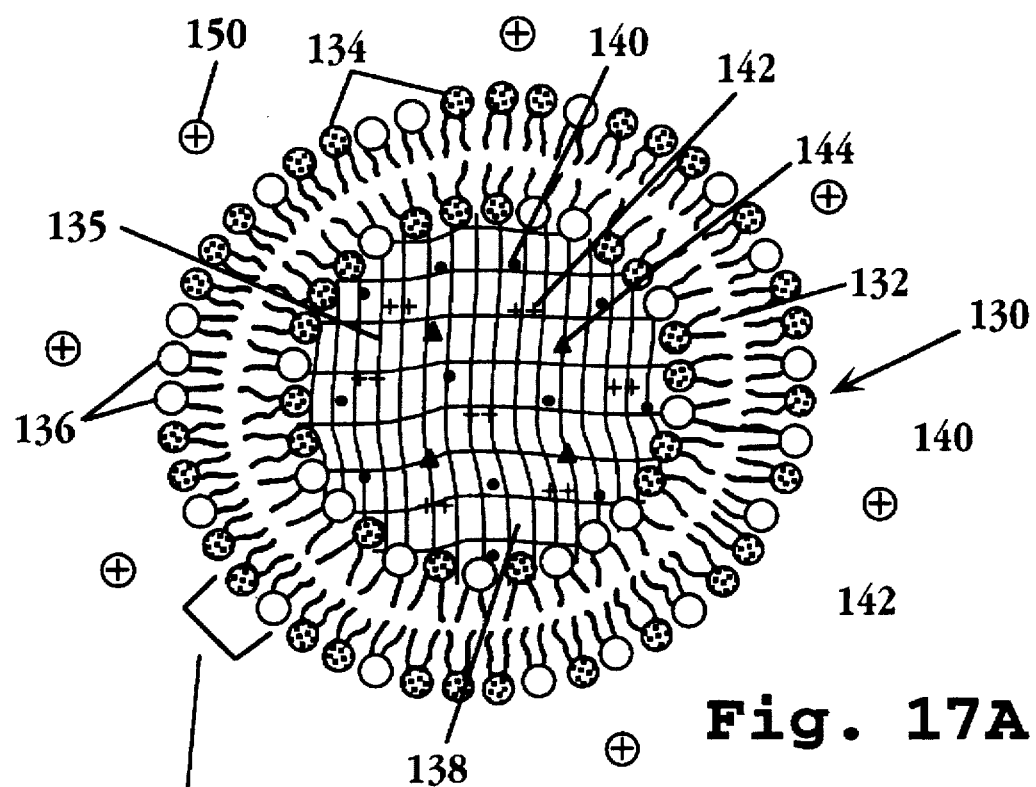
FIGS. 17A–17B illustrate an encapsulated microparticle containing specialized plasmalogen lipids that upon exposure to acid or reactive oxygen species are cleaved, resulting in perturbation of the external membrane and exposure of the decondensed microparticle to monovalent ions present in the extravesicular medium (FIG. 17B).
Figure 17B:
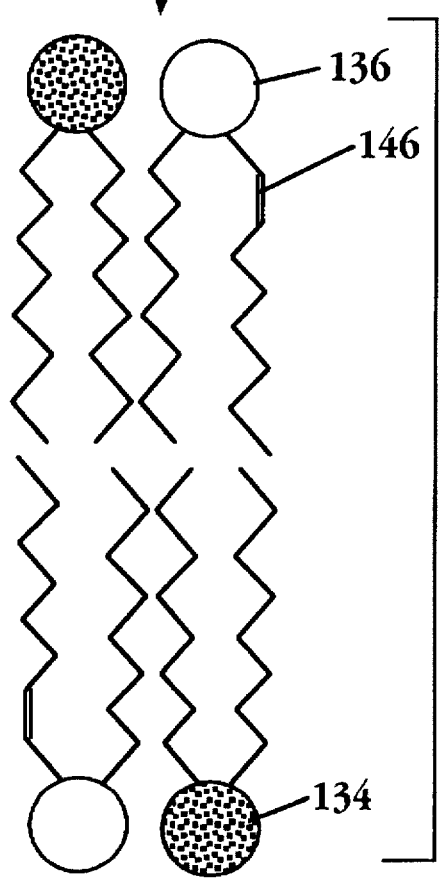
Figure 17C:
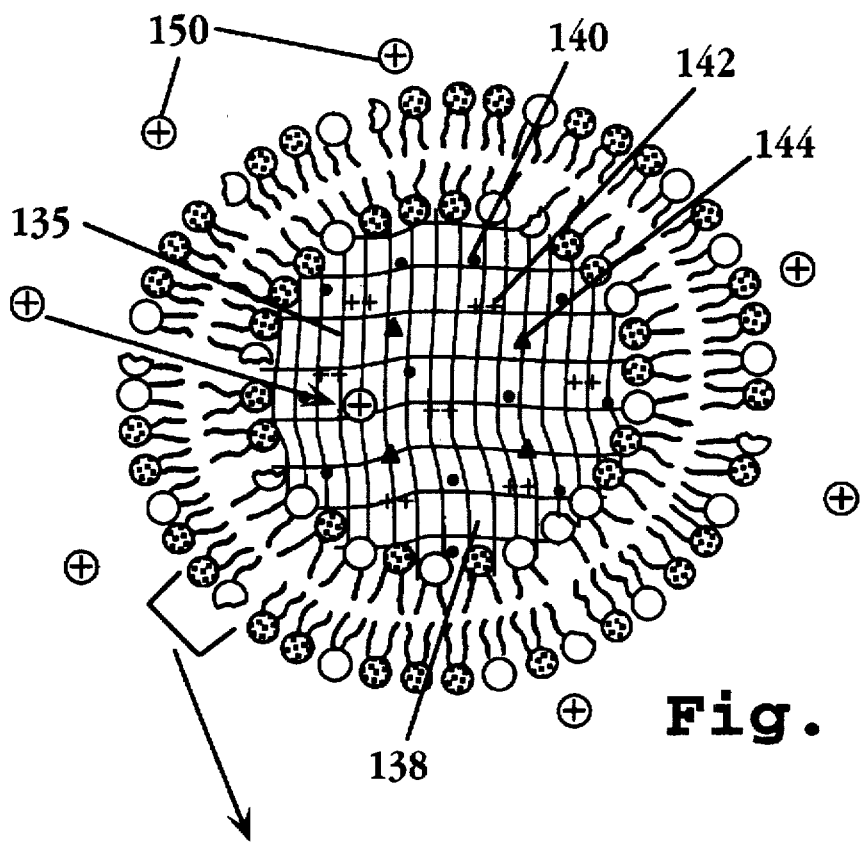
Figure 17D:
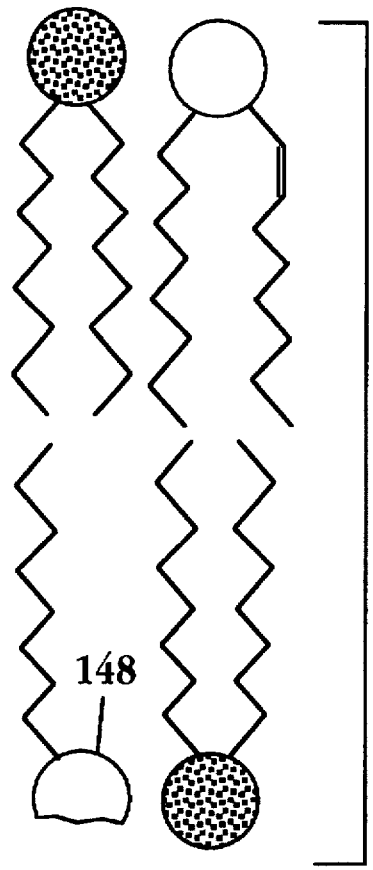

FIG. 17A shows a schematic drawing of an encapsulated microparticle 130 formed to include a plasmalogen lipid. Microparticle matrix 138 and incorporated drug compound 140 are encapsulated within bilayer vesicle membrane 132, which includes phospholipids 134 and plasmalogen phospholipids 136. Multivalent ions 142 maintain the microparticle in a condensed phase. Also shown in the matrix milieu are lysogenic compound molecules 144. Alternatively, lipophilic lysogenic compounds may be carried in the membrane bilayer.

Membrane 132 may be formed fully or partially of plasmalogen phospholipid, as illustrated. The ratio of plasmalogen phospholipids to conventional phospholipids (i.e., lipids such as phosphatidyl choline, phosphatidyl ethanolamine) present in the membrane may vary, according to the degree of sensitivity required. The membrane may, in addition, contain cholesterol and lipid derivatives effective to provide protection against first-pass loss to the reticuloendothelial system, in accordance with known principles of liposomal drug delivery. As the proportion of plasmalogen present membrane increases, the responsiveness to an activating stimulus increases.

As shown in the inset to FIG. 17A, plasmalogen vinyl ether groups 146 are preferably situated close to either the external face of the membrane (external membrane interface 140), or to the internal face of the membrane (internal membrane interface 142). This configuration provides access by the extra- and or intravesicular milieu to the reactive functional group, allowing for activation from either side of the membrane. As further illustrated in FIG. 17, exposure to acid or to reactive oxygen species (ROS) results in cleavage of vinyl ether functional groups in plasmalogen molecules, producing monoalkylated products 148. Both acid and ROS induce direct breakage of vinyl ether linkages. In one preferred embodiment, ROS are generated in situ by application of ionizing radiation, such as is induced by X-rays, to the target area, as described below.

Photoillumination can be used to generate ROS or acid and activate cleavage, when a lysogenic substance, such as a photoactivatable dye 144 is added to the encapsulated microparticle composition. Photoactivatable dyes known in the art include phenothiazinequinones ($\lambda_{max}$ 650–850 nm), purpurins (690–780 nm), phthalocyanines (670–710 nm), sulfonated naphthalocyanines (730–780 nm), octaalkoxy phthalocyanines (660–780 nm), and clorins (740–770 nm). Such dyes, when exposed to an appropriate wavelength of light, produce reactive oxygen species, such as singlet oxygen, hydroxyl radical, hydrogen peroxide and superoxide radicals. These reactive oxygen species are also effective to cleave vinyl ether linkages. Alternatively, the lysogenic substance can be one that produces acid in response to photoillumination. Examples of such lysogens include 4-formyl-6-methoxy-3-nitrophenoxyacetic acid, triarylsulfonium salts, and dibenzenesulfonyldiazomethane derivatives.

Cleavage of vinyl ether functional groups in response to a stimulus results in perturbations of the vesicle membrane. Such perturbations produce areas of leakiness in the membrane that allow passage of monovalent ions 150 across the membranes. As monovalent ions pass through the membrane to the intravesicular compartment the encapsulated microparticle 138 decondenses. This decondensation accelerates breakdown and eventual rupture of the membrane, and results in release of compound 140 to the extravesicular environment, as shown.

In still another embodiment, lipids contained in the bilayer membrane of the particle composition may include a light sensitive lipid, as described in U.S. Pat. No. 4,882,165, incorporated herein by reference. Light sensitive lipids absorb light at a selected wavelength to change conformation to a modified structure. When present in a membrane lipid bilayer of a vesicle, formation of the modified lipid structure results in perturbation of the bilayer, causing leakiness and rupture of the encapsulated microparticle, as discussed above. A suitable light sensitive lipid includes an amphipathic lipid having covalently attached to one or more of its alkyl sidechains light sensitive groups. Examples of this type of compound include di-retinoyl-sn-glycero-3-phosphocholines, phospholipids having light-sensitive retinoyl groups at the terminal end of one or both of its sidechains. Compounds of this class can be prepared according to the reaction schemes described in U.S. Pat. No. 4,882,165. These compounds change conformation at wavelengths from about 300 to 400 nm, preferably about 360 nm.

C. Amplified Compound Release

Figure 14A:
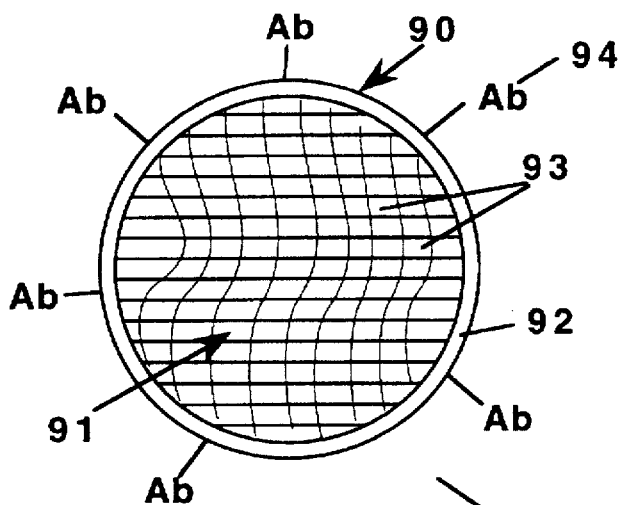
FIGS. 14A–14C illustrate the activation of an encapsulated microparticle like that shown in FIG. 13 (14A) by cell lysis in the presence of antigen and complement (14B), and the cascade of events leading to rapid release of entrapped compound in the microparticle's matrix (FIG. 14C)
Figure 14B:
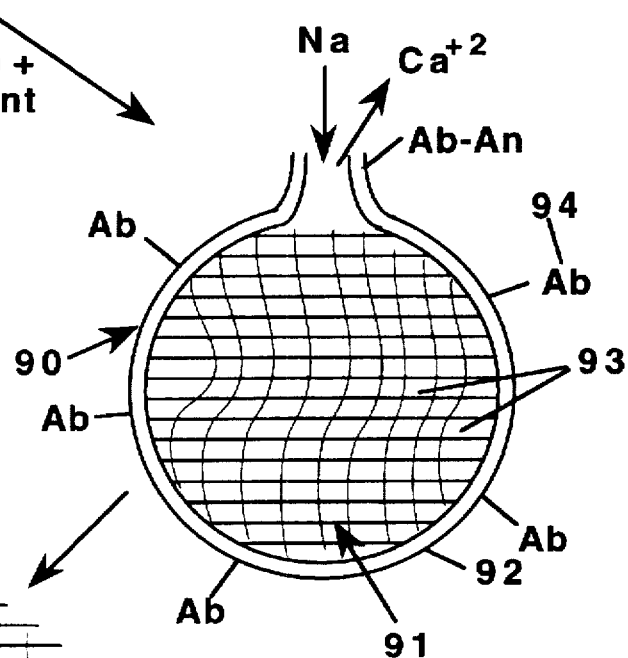
Figure 14C:
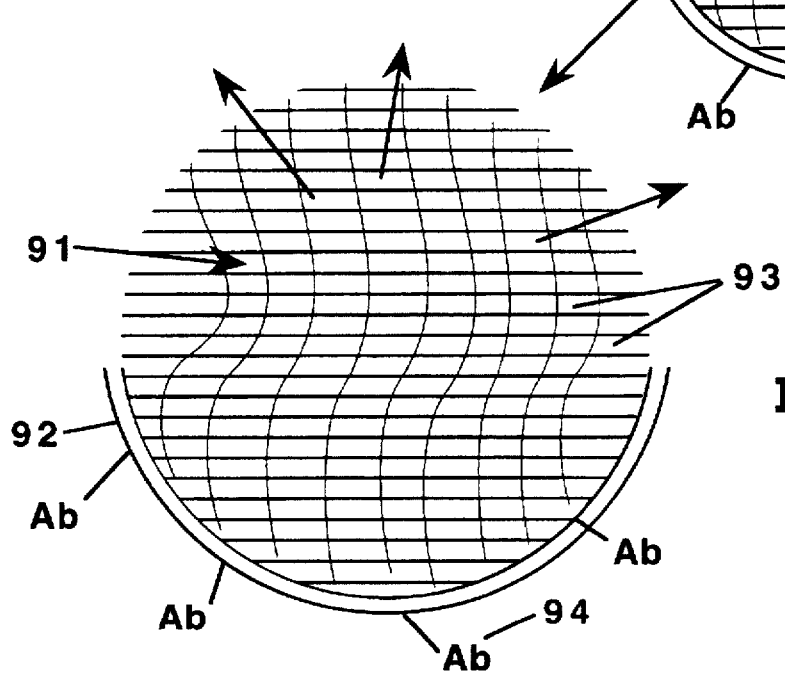

The encapsulating lipid membrane is designed to respond to the selected target stimulus, by allowing an influx of monovalent counterions, such as $Na^+$ present in the environment, and an efflux of internal multivalent counterions, through localized areas of membrane lysis. FIGS. 14A–14C illustrate the mechanism of amplified, cascade-type compound release from the particle composition of the invention. FIG. 14A shows an encapsulated microparticle 90 similar to the one shown in FIG. 13, having a condensed-phase microparticle 91 encapsulated in a lipid bilayer membrane 92. Entrapped compound in the condensed matrix is indicated at 93. The membrane has surface-attached anti-ligand antibody or $F_{ab}$ antibody fragments molecules 94 effective to bind to target-site ligand molecules.

The target stimulus that stimulates compound release from the particles is binding of the target-site anti-ligand molecules, such as an antigen (An), to the surface-bound antibodies. Where the composition is used for in vivo delivery of a therapeutic compound, the triggering binding event for compound release may occur at a bloodstream target site, or at a tissue site, e.g., at a site involving cell- or tissue-specific surface antigens.

Where the composition is designed to be used as a homogeneous-assay diagnostic reagent, as described below, the target site is a sample mixture containing a ligand analyte in solution.

Binding of the antigen to the surface-bound anti-ligand molecules, in the presence of blood complement components, leads to localized membrane lysis or rupture, as indicated in FIG. 14B. The areas of localized lysis allow influx of monovalent counterions, such as $Na^+$ and $K^+$, and efflux of encapsulated multivalent counterions, such as $Ca^{+2}$ or histamine. The monovalent counterions are present in a physiological environment, in a drug-delivery setting, or are included in the reaction medium, in an analyte assay.

This exchange of counterions across the membrane, at the point of localized lysis, produces a rapid localized decondensing of the encapsulated particle matrix, further rupturing the vesicle membrane and leading to increased counterion exchange.

The initial localized lysis thus sets off a cascade of events which lead to rapid swelling i.e., decondensing of the entire microparticle matrix, as illustrated in FIG. 14C. This mechanism is an amplified or cascade type mechanism, in that a small localized signal at the vesicle membrane is amplified by localized matrix swelling until the entire matrix has decondensed. The rapid decondensing acts to expel a portion of the entrapped compound and allows remaining drug molecules to diffuse into the surrounding medium, as shown in FIG. 14C. The series of events from localized lysis to complete swelling of the encapsulated matrix, preferably occurs in a period between about 1–10 sec or less.

Figure 15A:
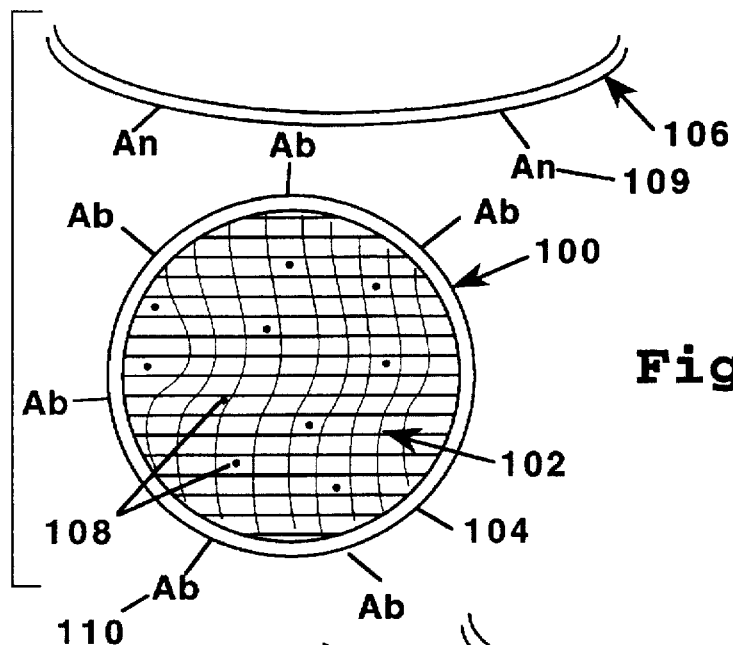
FIGS. 15A–15C illustrate attachment of an encapsulated microparticle (FIG. 15A) like that in FIG. 13 to the surface of a cell, with fusion of the microparticle and cell membrane (15B), and rapid decondensing of the microparticle's polymer matrix to release entrapped drug into the interior of the cell (15C)
Figure 15B:
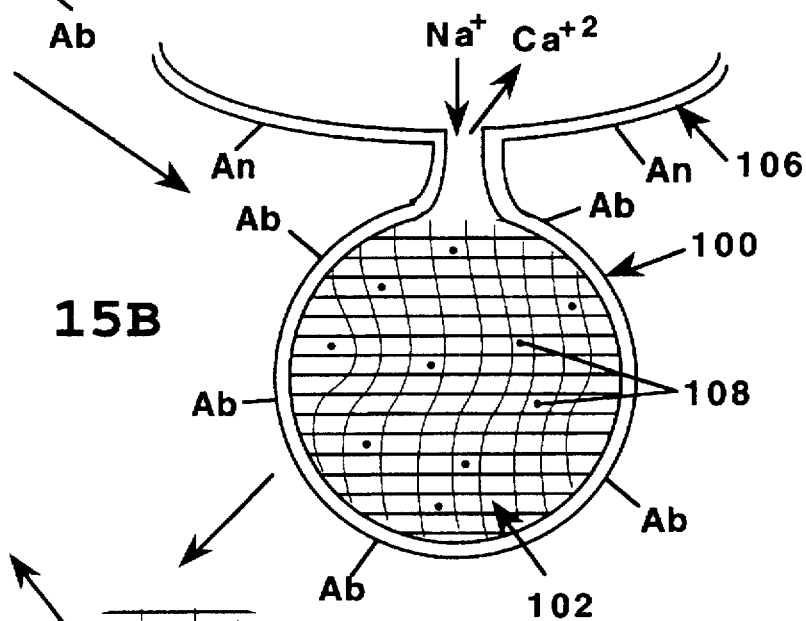
Figure 15C:
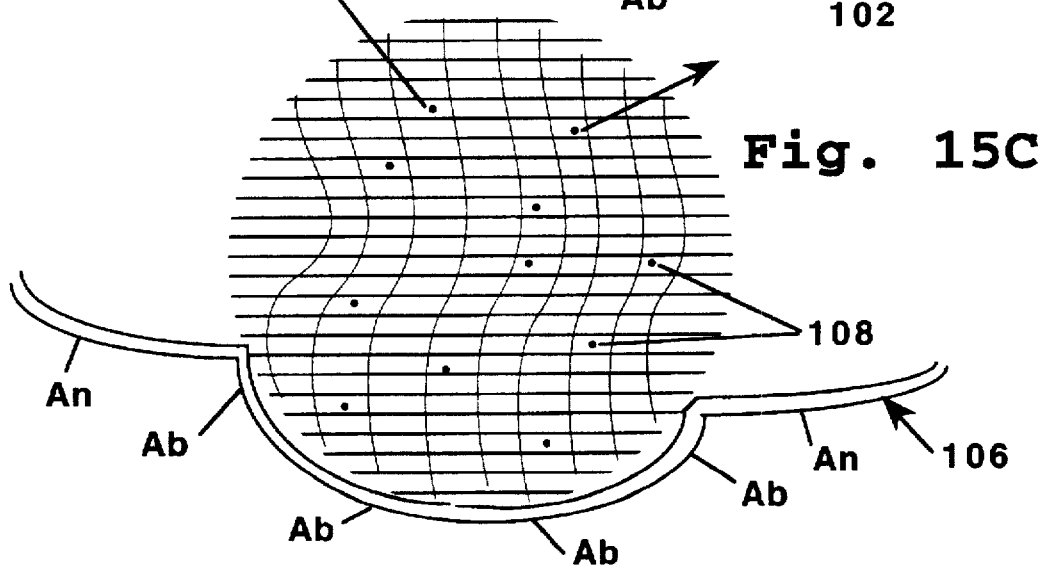

FIGS. 15A–15C illustrates rapid target-initiated compound release from a composition particle 100 at a target surface site, such as shown at 106. The encapsulated microparticle is composed of a condensed-phase matrix 102 having entrapped compound 108 and an encapsulating lipid bilayer membrane 104. The membrane contains surface bound anti-ligand molecules 110, such as antibody or antibody fragment molecules.

The target surface shown here is a cellular surface having surface-specific anti-ligand molecules 109, for use in targeting an in vivo cell surface site. As illustrated in FIG. 15B, this binding leads to localized fusion of the particle membrane with the cell membrane. The areas of localized lysis allow influx of monovalent cations, such as $Na^+$ and $K^+$, and efflux of encapsulated divalent cations, such as $Ca^{+2}$ or histamine, causing rapid decondensing of the encapsulated particle matrix, further rupturing the vesicle membrane and leading to increased cation exchange effects.

As above, initial localized lysis sets off a cascade of cation influx and matrix swelling that leads to rapid and complete expansion, i.e., decondensing of the microparticle, as illustrated in FIG. 15C, expelling entrapped drug into the target cell.

Where the composition is used as a diagnostic reagent in a solid-phase assay, the binding surface in FIG. 15A may be a solid-support surface having a surface-bound anti-ligand molecules capable of binding to the particle anti-ligand molecules, to bind the particles to the surface, in proportion to the amount of analyte also present in the reaction mixture. After washing the surface, to remove non-specifically bound material, the particles can then be lysed, e.g., by heating or hypoosmotic swelling, to release the compound, e.g., reporter molecule, contained in the particles.

D. Drug-Release Compositions

1. Administration of Therapeutic Compounds in Encapsulated Microparticles

In one general embodiment, the compositions of the invention serve as drug delivery vehicles, for particle delivery to a selected in vivo site, with rapid release of the entrapped therapeutic agent at the site. The selected site is typically within the bloodstream or a localized site accessible by the bloodstream.

For use in treatment, a suspension of microparticle vesicles of the type described above is administered, typically by parenteral administration, to reach a selected target site which can include circulating antibodies, specific cells, organs or tissues, or a solid tumor site.

For parenteral administration, and in particular for intravenous administration in bolus form, the method allows higher drug doses to be administered because the drug may be present within the vesicles at concentration well above the drug's normal solubility, which may limit drug dosage in free form, or in conventional liposome-encapsulated form. Further, since the drug is not released until it reaches a target site, side effects due to generalized distribution of free drug are reduced. More particularly, compositions formed in accordance with the invention can be used to deliver therapeutic compounds to in vivo target site having a selected pH, temperature, ligand concentration or binding-molecule characteristics, as discussed in relation to the specific compositions below. Such therapeutic compositions will generally have an average size between 0.05 and 0.5 microns.

Another important advantage of the method is the ability to achieve rapid, controlled drug release at a target site. Following vesicle administration, a portion of the vesicles localize at the target site in vivo, where the vesicles undergo partial lysis in response to selected conditions at the site, leading to a cascade of monovalent cation influx and divalent cation efflux, as described above, with rapid release of the entrapped drug at the site. This is in contrast, for example, to conventional lipid-vesicle drug delivery, where vesicles disintegration and drug leakage occurs slowly over an extended vesicle-circulation time.

2. Administration of Antibody-Modified Compositions

Encapsulated microparticles having surface-attached anti-ligand antibodies or $F_{ab}$ fragments are particularly useful in delivering therapeutic compositions to those cells or tissues that have a specific antigenic characteristic to which the anti-ligand molecules are directed. Examples of target cells include specific blood cell types, such as $CD34^+$ cells, tumors exhibiting characteristic tumor antigens and the like. Lysis at the target cell is facilitated by perturbations of the vesicular membrane upon antibody attachment or complement fixation that occurs particularly when the anti-ligand molecule is an IgM or an IgG antibody.

The preferred route of administration of antibody-modified compositions will depend upon the location of the target tissue. Generally, parenteral administration to the bloodstream is preferred. The dosage of compound is calculated according to standard pharmaceutical principles in view of the relative mass of the tissue to be treated, the size of the subject, the amount of compound to be delivered, the avidity of the antibodies for binding to the target antigen and estimated clearance rates of the compositions. Estimates of clearance rates and efficiency of targeting can be made, based on preliminary tests in standard experimental models known in the art.

3. Administration of Ion-Channel Modified Compositions

Compositions of the invention incorporating particular ion channels are preferably used to target areas having characteristics that trigger selective opening of the channels. For example, compositions containing glutamate channels are particularly useful in targeting therapeutics to areas associated with high levels of glutamate such as neuronal or glial cells. Areas of the brain that have been subjected to ischemia or anoxia are associated with particularly high levels of glutamate. Accordingly, glutamate-gated sodium or potassium channel-containing encapsulated microparticles may be directed to these regions for release of therapeutic compounds, such as calcium channel blockers or NMDA antagonists useful in reducing ischemic damage.

Likewise, calcium-activated potassium channels, such as described herein may find use in treatment of disorders characterized by local regions of excess calcium. Examples of such disorders include myocardial infarction and cerebral ischemia, where damaged cells are known to release calcium into the local environment. Delivery of encapsulated microparticles to these regions can be effected via the bloodstream or through a catheter introduced to the region according to methods known in the art to be compatible with delivery to the target of choice. Encapsulated microparticles may also be directed to brain regions through intracerebroventricular or intrathecal means.

Acetylcholine receptor-modified compositions are used to trigger release of microparticle contents at target sites where acetylcholine is released, such as the neuromuscular junction, the ganglia, and in acetylcholine-rich regions of the brain, such as the hippocampus. Such compositions may be used, for example, in the treatment of such neuromuscular disorders as Myasthenia gravis or to effect specific ganglionic blockade.

The preferred route of administration of ion channel-modified compositions will depend upon the location of the target tissue. Generally, parenteral administration to the bloodstream is preferred; however, for treatment of muscular disorders, intramuscular injection may be advantageous. Likewise, intrathecal or intracerebral injection may best facilitate delivery of compositions to the brain. The dosage of compound is calculated according to standard pharmaceutical principles in view of the relative mass of the tissue to be treated, the size of the subject, the amount of compound to be delivered, and estimated clearance rates of the compositions. Estimates of clearance rates and efficiency of targeting can be made, based on preliminary tests in standard experimental models known in the art.

4. Administration of Compositions Having Selected Lipid Components

Encapsulated microparticles having specialized lipids can be used in a number of therapeutic settings. Lipids are selected in accordance with the invention to alter in conformation or structure when exposed to one or more of a variety of stimuli, including heat, light, high-energy irradiation, free radicals, changes in pH, or presence of phospholipase enzymes.

a. Temperatures-Sensitive Encapsulated Microparticles

In one specific embodiment, the outer membrane of the encapsulated microparticle is formed using lipids having a phase transition temperature between the normal body temperature and the elevated temperature. Such microparticles will also include a selected therapeutic compound in the microparticle matrix. The composition is administered, preferably by parenteral injection to the bloodstream. In accordance with known circulation and clearance properties of circulating liposomes, the microparticle composition will accumulate in certain organs, such as the reticuloendothelial system (liver, spleen, lymph) as well as at highly vascularized tumor sites and sites of inflammation. This property of the circulating liposomes can be used, in conjunction with the temperature-sensitive microparticle composition, to induce selective release at one or more of the accumulation sites, or to effect release at a specific vascularized region, by selectively heating the particular organ or region to a temperature corresponding to the phase transition temperature of the lipids comprising the liposomal membrane.

One exemplary use of such a temperature-sensitive composition is in the treatment of one or more forms of arthritis. Liposomes are known to accumulate in inflamed joint regions during the normal circulation process. Release of compound is induced by heating of the joint region, using conventional techniques. This treatment method is particularly advantageous for delivery of such gold-containing drugs as aurothioglucose and auranofin, whose general toxicity limit administration by conventional means.

b. Microparticles With Selected Lipids

As described in Section V.B.3 above, encapsulated microparticle compositions that include lipid components, such as plasmalogen lipids, can be stimulated to lyse and release their contents in response to such stimuli as acid and reactive oxygen species. Such compositions are useful in a variety of therapeutic applications. In one embodiment, the composition is directed to areas of high acidity, particularly intracellular lysosomes. In this embodiment, the particles of the composition are designed for targeting to cells capable of taking up particles by phagocytosis or endocytosis, with eventual intracellular processing of the particles in the lysosomes of the cells. In the acidic environment of the lysosomes, the lipid conformation or stability is altered to permit influx of monovalent ions in the environment, and release of particle-entrapped compound intracellularly. Alternatively, the target trigger may be phospholipase enzyme present in the lysosomes, and active against lysophospholipid components present in the particle bilayer membranes.

In another embodiment, plasmalogen-containing compositions are used in delivering a therapeutic compound to areas that can be selectively irradiated to form radical oxygen species in situ. In this modality, a dose of ionizing radiation is directly administered to produce reactive oxygen species at the target site.

In this context, the term "ionizing radiation" includes electromagnetic radiation having a wavelength in the range from about 400 nm (4000 Å) to about 0.1 pm (0.001 Å). Ionizing radiation includes ultraviolet light (~400 nm to ~10 nm), x-rays (~10 nm to ~10 pm), and gamma-rays (~10 pm to ~0.1 pm). For the purposes of the invention, "ionizing radiation" refers particularly to those types of ionizing radiation used in imaging of internal organs or cancer therapy, specifically, gamma rays and X-rays. These types of radiation are characterized by high frequency electromagnetic rays of relatively short wavelength and are capable of deep tissue penetration and moderate ionization of the tissues along their pathways. Such radiation is generally administered using a directed source emitter, such as an X-ray machine.

Ionizing radiation also includes radiation consisting of subatomic particles, such as electrically charged alpha particles, protons, electrons and electrically uncharged neutrons that are emitted by radionuclides suitable for administration to humans in trace quantities, in some cases in association with a carrier molecule, according to methods known in the art. Such radionuclides include, but are not limited to, technicium-99m, iodine-131, gallium-67, and indium-111. The particles produced by these compounds produce dense ionization of structures and molecules along their pathways in tissues; however, depth of penetration is limited and varies as a function of subatomic particle size, charge and velocity.

In the context of the present invention, this radiation from subatomic particles can be directed to a particular body region, for example, by attaching a radionuclide to a carrier molecule such as an antibody, directed to the particular region, or by encompassing the radionuclide in a liposome having on its surface a site directed antibody, for release at the target region. When the radionuclide accumulates in the region of interest, it induces production of ROS, which in turn stimulate lysis of plasmalogen-containing compositions of the invention at the specific therapeutic site. Compositions of this type find particular utility in treatment of solid tumors and other regions generally characterized by high levels of vascularization and vascular permeability.

In general, the dose of ionizing radiation absorbed by a sample can be expressed in units of rad or Gray. A rad, which is equal to 1 cGy (centigray), is equal to 100 ergs per gram of sample (i.e., an amount of energy imparted to the sample per sample unit mass). Appropriate doses of radiation and tissue damage produced by standard ionizing radiation sources are well known to practitioners in the art.

In one specific embodiment, plasmalogen-containing compositions can be used to deliver anti-thrombotic agents, such as streptokinase, tissue plasminogen activator and urokinase, to areas of vascular thrombosis. Following administration, the area is irradiated to induce release of compound at the site of thrombosis.

Similarly, plasmalogen-containing compositions of the invention can be used in certain X-ray imaging applications. In one general method, an X-ray-opaque compound (contrast medium) is entrapped in the condensed phase of the microparticle matrix and is encapsulated with a plasmalogen containing lipid membrane, as discussed herein. The resulting composition is then administered to the subject, in accord with known pharmaceutical principles discussed above. A dose of X-irradiation is then directed to the body structure, including tumors, organs and the like. The radiation produces ROS at the specific site, resulting in selective release of compound release from the particles that have accumulated at the site. This method is particularly useful in imaging areas characterized by high vascularization, and more particularly, tumors and other regions, such as inflamed areas, characterized by increased capillary permeability. This method also allows for temporal monitoring of release of imaging agent at the site of interest.

In another related method, plasmalogen-containing encapsulated microparticle compositions can be used to measure free radical activity in a selected region of the body. In this method, the microparticles will include a reporter molecule, the release of which can be measured in tissues of interest to determine oxidative activity. This method can also be used to deliver to sites of elevated oxidative activity free radical or activated oxygen quenchers such as superoxide dismutase.

Plasmalogen-containing encapsulated microparticle compositions can also be activated to release their contents by photoillumination, when the composition further includes a lysogenic substance that, in response to photoillumination at a pre-determined wavelength, produces ROS or acid. As discussed above, such compounds then stimulate lysis of the vesicular membrane and result in expulsion of microparticle contents to the external medium. Lysogenic photosensitive compounds are well known in the art, and include but are not limited to photoactivatable dyes, such as phenothiazinequinones, purpurins, phthalocyanines, sulfonated naphthalocyanines, octaalkoxy phthalocyanines and clorins, and acid-producing light sensitive lysogens such as 4-formyl-6-methoxy-3-nitrophenoxyacetic acid, triarylsulfonium salts, and dibenzenesulfonyldiazomethane derivatives. Each of the foregoing compounds is stimulated by a known wavelength of light.

According to one embodiment of the invention, encapsulated microparticle compositions carrying one or more of these photoactivatable compounds and a selected therapeutic agent is given to a subject. The particles then accumulate at specific areas, in accordance with known principles of liposomal circulation and accumulation. Selective release of particle-associated contents of the encapsulated microparticles is accomplished by illuminating the region to be treated with the appropriate wavelength of light. For example, when the lysogen is one of the phenothiazinequinones, the light source will be tuned to deliver light of a wavelength between 650 and 850 nm, depending on the particular compound used. Alternatively, when the lysogen is the purpurin bacteriochlorophll a, activation is by photoillumination at 780 nm.

This method finds use in a variety of applications. One such application is the treatment of psoriasis. Antipsoriatic compounds such as psoralins, glucocorticoids, coal tar, anthralin, methotrexate, or etretinate can be delivered to psoriatic regions of the skin, which, due to the associated inflammation and increased capillary permeability, selectively accumulate liposomes and microparticles. The region is then illuminated with the appropriate wavelength of light to effect excitation of the photoactivatable lysogen carried in the encapsulated microparticle. In response to the light stimulus, the lysogen produces ROS or acid, according to its particular characteristics. As discussed above, such ROS or acid is effective to stimulate lysis of the microparticle vesicular membrane and release of the therapeutic compound in the target site. In this particular method, the composition will generally be administered by parenteral injection to the bloodstream. Alternately the microparticle composition can be formulated in a cream or ointment for activation by light source or sunlight. The dose and mode of administration will be determined by the practitioner in accordance with general pharmaceutical principles, discussed above, in view of the size and severity of the psoriatic lesion.

In other therapeutic applications, photoactivated release, photoillumination may be selectively delivered to a region by catheter, such as by a laser catheter, according to methods known in the art. This mode of treatment can also be applied to vascular thromboses, as discussed above. Another general application for photoillumination-induced release of compounds from encapsulated microparticles is a light-activated drug release device, such as a transdermal device. Encapsulated microparticles formulated in accordance with the invention and including a photoactivatable lysogen are specifically formulated for slow or extended release. In this application, the plasmalogen content of the membrane encapsulated microparticles will be low (less than about 10–25%) relative to the conventional phospholipid content. Alternatively, or in addition, a mixture of compositions ranging from 5–100% plasmalogen membrane content can be used. The composition is formulated in a transdermal patch having a transparent or translucent upper light-admitting region that allows for exposure of the encapsulated microparticle composition to light. The light-admitting region can be selectively covered or uncovered expose the composition to light, as required for delivery of compound in a controlled manner.

The following example illustrates a method for isolating biological microparticles useful in the invention.

Isolation of Mast Cells

Mast cell secretory granules were prepared from adult beige ($bg^j/bg^j$) mice (Jackson Laboratories, Bar Harbor, Me.) according to standard methods described by Monck et al., (1991), and modified to increase the number of intact isolated secretory granules. Cells were obtained by peritoneal lavage with a solution of the following composition (in mM): 136 NaCl, 1 $MgCl_2$, 2 $CaCl_2$, 22 $NaHCO_3$, 0.4 $K_2HPO_4$, 2 Glucose, 8.8 units/ml Heparin, 0.1% Bovine serum albumin (300 mOsm/kg, pH 7.3). Cells were resuspended in 1 ml, layered on 2 ml 22.5% wt/vol metrizamide and centrifuged at room temperature for 20 min. at 400 g. The pellet was resuspended in 1 ml of a $Ca^{2+}$, $Mg^{2+}$-free sonication buffer of the following composition (in nM): 130 NaCl, 10 KCl, 22 $NaHCO_3$, 0.3 $K_2HPO_4$, 0.1% Bovine serum albumin (300 Mosm/kg, pH 7.3). This suspension of purified mast cells was subjected to 4 sonication pulses at 25% of maximum power (sonicator model 45; Branson Sonic Power Co., Danbury, Conn.) and plated onto glass bottomed chambers and stored at 37° C. under 5% $CO_2$ atmosphere until use. An average of about 200 intact secretory granules per mouse were routinely obtained, that were osmotically stable with a half-life of over 3 h.

Isolated secretory granules were bathed in a standard solution containing (in mM): 25 NaCl, 125 Kcl, 2 $CaCl_2$, 1 $MgCl_2$, 0.2 ATP, 10 HEPES (300 Mosm/kg, pH 7.3).

Alternatively, mast cells were collected in a solution containing 150 mM NaCl, 10 mM Hepes, 3 mM KOH, 0.943 mM NaOH, 1 mM $MgCl_2$, 2 mM $CaCl_2$, and 12 mM glucose, 310 mmol/kg, pH 7.3, at room temperature. Secretion was stimulated by 10 ug/ml of compound 48/80 (Sigma Chemical Co., St. Louis, Mo.). Swelling of secretory granules was recorded using a Toshiba video camera (model IKC30M) mounted on an IM35 microscope (Zeiss) equipped with Nomarski optics including a 63× oil immersion Zeiss objective. (3500×, final magnification). The diameter of the granules was measured by single frame video image analysis at a sample rate of 30 frames/sec. Single frame images were played back from a VCR (BV-1000 Mitsubishi) and sampled by a frame grabber (DT 2851, Data Translation) operated by the Image-Pro software package (Media Cybernetics). Volumetric expansion was calculated assuming a spherical shape for the secretory granules. Size is conveniently expressed as a percent of final decondensed volume after exocytosis in external solution (pH 7.3). Granules were re-condensed to within 5% of pre-secretion volume by bathing in a solution containing 50 mM histamine, pH 3, devoid of other ions.

While the invention has been described with respect to particular compositions and method, it will be appreciated that various changes and modifications may be made without departing from the invention.

It is claimed:

1. A composition for release of a compound upon exposure to a target stimulus selected from the group consisting of pH, temperature, radiation, a ligand and an ion-channel activator, comprising encapsulated microparticles having an average size between 0.05 and 5 microns, each encapsulated microparticle being composed of
   (i) an external lipid bilayer membrane effective to allow influx of external ions into the particle interior when exposed to said target stimulus,
   (ii) encapsulated within the lipid membrane, a condensed-phase microparticle which is composed of a matrix of crosslinked polyionic polymer filaments, and which is capable of decondensing to an expanded state when multivalent counterions also present within the matrix are replaced by monovalent counterions, and
   (iii) the compound to be released entrapped in the microparticle matrix, with said matrix in its condensed phase, whereby localized perturbation of the lipid membrane, and influx of monovalent counterions into the microparticle matrix, in response to said target stimulus, causes swelling and compound release from said microparticles.

2. The composition of claim 1, wherein the microparticles have an average size 0.05 and 0.5 microns, the compound is a therapeutic compound, and the lipid membrane is effective to allow influx of external counterions into the microparticle matrix when exposed to said target stimulus in vivo.

3. The composition of claim 2, wherein the polymer filaments forming the microparticle matrix are sulfated, sulfonated, carboxylated, or polyphosphated polyanionic polymers, and the multivalent counterion is a multivalent cation.

4. The composition of claim 3, wherein the filaments forming the microparticle matrix are comb-polymer glycoprotein filaments.

5. The composition of claim 2, wherein the halflife of matrix swelling, following localized perturbation of the membrane, is less than about 1 sec.

6. The composition of claim 2, wherein said microparticle matrix contains less than about 30 volume percent of an aqueous medium and said therapeutic compound is at a concentration which exceeds its solubility in the aqueous medium.

7. The composition of claim 2, which further comprises anti-ligand molecules attached to the eternal lipid-membrane surfaces of said encapsulated microparticles, for binding specifically to antigen or antibody molecules present at such in vivo site.

8. The composition of claim 2, wherein said target stimulus is heat and said lipid bilayer membranes are formed of lipids having a phase transition temperature above normal body temperature.

9. The composition of claim 2, for delivering said compound to a target region containing an activator for an ion channel protein, wherein said lipid membrane further comprises an ion-selective channel.

10. The composition of claim 9, wherein said ion channel is a calcium-activated ion channel.

11. The composition of claim 10, wherein the ion channel is a calcium-activated potassium channel.

12. The composition of claim 9, wherein said ion channel is a ligand-gated ion channel.

13. The composition of claim 12, wherein the channel is a glutamate receptor.

14. The composition of claim 12, wherein the channel is a nicotinic acetylcholine receptor.

15. The composition of claim 1, wherein the encapsulated microparticles' lipid membranes include a plasmalogen lipid having a vinyl ether functional group capable of cleavage in response to acidic conditions or a reactive oxygen species.

16. The composition of claim 15, wherein the encapsulated microparticle further comprises a lysogenic substance that, in response to photoillumination, produces a reactive oxygen species effective to cleave the vinyl ether functional group of the plasmalogen.

17. The composition of claim 15, wherein the microparticle matrix further comprises a lysogenic substance that, in response to photoillumination, produces acid effective to cleave the vinyl ether functional group of the plasmalogen.

18. The composition of claim 15, wherein the plasmalogen is 1-alk-1'-enyl-2-palmitoyl-sn-glycero-3 phosphocholine.

19. The composition of claim 1, wherein said lipid bilayer membranes include a light-sensitive lipid capable of changing conformation in response to exposure to light at a pre-determined wavelength.

20. The composition of claim 19, wherein the light-sensitive lipid is a retinoyl-sn-glycero-3-phosphocholine.

* * * * *